(12) United States Patent
Matsumoto et al.

(10) Patent No.: US 7,935,989 B2
(45) Date of Patent: May 3, 2011

(54) SINGLE-ELECTRON TRANSISTOR, FIELD-EFFECT TRANSISTOR, SENSOR, METHOD FOR PRODUCING SENSOR, AND SENSING METHOD

(75) Inventors: Kazuhiko Matsumoto, Tsukuba (JP); Koichi Mukasa, Sapporo (JP); Atsushi Ishii, Sapporo (JP); Seiji Takeda, Sapporo (JP); Makoto Sawamura, Sapporo (JP); Agus Subagyo, Sapporo (JP); Hirotaka Hosoi, Sapporo (JP); Kazuhisa Sueoka, Sapporo (JP); Hiroshi Kida, Sapporo (JP); Yoshihiro Sakoda, Sapporo (JP)

(73) Assignees: Japan Science and Technology Agency, Kawaguchi-shi (JP); National Institute of Advanced Industrial Science and Technology, Tokyo (JP)

( * ) Notice: Subject to any disclaimer, the term of this patent is extended or adjusted under 35 U.S.C. 154(b) by 1046 days.

(21) Appl. No.: 10/558,063

(22) PCT Filed: May 21, 2004

(86) PCT No.: PCT/JP2004/007300
§ 371 (c)(1),
(2), (4) Date: Aug. 15, 2006

(87) PCT Pub. No.: WO2004/104568
PCT Pub. Date: Dec. 2, 2004

(65) Prior Publication Data
US 2006/0273356 A1   Dec. 7, 2006

(30) Foreign Application Priority Data
May 23, 2003  (JP) ................................ 2003-146480
Feb. 16, 2004  (JP) ................................ 2004-037866

(51) Int. Cl.
*H01L 29/772*   (2006.01)

(52) U.S. Cl. .................................... 257/253; 257/E51.04
(58) Field of Classification Search .................... 257/40, 257/213, 252, 253, 414, E51.001, E51.024, 257/E51.038, E51.04
See application file for complete search history.

(56) References Cited

U.S. PATENT DOCUMENTS
4,180,771 A    12/1979  Guckel
4,238,757 A  * 12/1980  Schenck ........................ 257/253
(Continued)

FOREIGN PATENT DOCUMENTS
JP           58-19984 B2      4/1983
(Continued)

OTHER PUBLICATIONS

Kazuhiko Matsumoto ("Carbon Nanotube O Mochita Ryoshi Koka Nanodevice No Shusekika Gijutsu O Kaihatsu," Sep. 13, 2002, National Institute of Advance Industrial Science and Technology (AIST) press release.*
International Search Report Dated Aug. 24, 2004, Four (4) Pages.
Kazuhiko Matsumoto, "Ichi Seigyo Seicho Carbon Nanotube No Sakusei to Device Oyo", Oyo Butsuri, Mar. 10, 2003, vol. 72, No. 3, p. 331 to 332.

(Continued)

*Primary Examiner* — Minh-Loan T Tran
*Assistant Examiner* — Kevin Quinto
(74) *Attorney, Agent, or Firm* — Crowell & Moring LLP

(57) ABSTRACT

A single-electron transistor comprising at least a substrate, a source electrode and a drain electrode formed on top of the substrate opposing to each other, and a channel arranged between the source electrode is disclosed wherein the channel is composed of ultra fine fibers. By having such a constitution, a sensor can have excellent sensitivity.

5 Claims, 36 Drawing Sheets

U.S. PATENT DOCUMENTS

| | | | | |
|---|---|---|---|---|
| 5,140,393 | A | * | 8/1992 | Hijikihigawa et al. ........ 257/252 |
| 2002/0117659 | A1 | * | 8/2002 | Lieber et al. .................... 257/14 |
| 2003/0134433 | A1 | * | 7/2003 | Gabriel et al. ................ 436/518 |
| 2003/0148562 | A1 | * | 8/2003 | Luyken et al. ................ 438/197 |
| 2003/0214054 | A1 | * | 11/2003 | Awano et al. ................. 257/797 |

FOREIGN PATENT DOCUMENTS

| | | |
|---|---|---|
| JP | 2002-118248 A | 4/2002 |
| WO | WO 01/44796 A1 | 6/2001 |
| WO | WO 02/48701 A2 | 8/2002 |

OTHER PUBLICATIONS

Kazuhiko Matsumoto, "Carbon Nanotube O Mochita Ryoshi Koka Nanodevice No Shusekika Gijutsu O Kaihatsu", [Online], Sep. 13, 2002, National Institute of Advance Industrial Science and Technology (AIST) Press Release, Jul. 9, 2004.

Kazuhiko Matsumoto, "Ichi Seigyo Seicho Carbon Nanotube Ni Yoru Tan'Itsu Denshi Soshi Oyobi Denshi Hoshutsu," 2002 Nen Shuki Dai 63 Kai The Japan Society of Applied Physics Gakujutsu Koenkai Yokoshu, Sep. 24, 2002, p. 13.

* cited by examiner

SINGLE-ELECTRON TRANSISTOR, FIELD-EFFECT TRANSISTOR, SENSOR, METHOD FOR PRODUCING SENSOR, AND SENSING METHOD

FIELD OF THE INVENTION

The present invention relates to a sensor, and particularly relates to a sensor such as a biosensor having a structure of a field-effect transistor (hereinafter abbreviated to FET) or a single-electron transistor (hereinafter abbreviated to SET).

BACKGROUND ART

In a biosensor proposed in the background art, a membrane having a reactive group selectively reacting to a specific molecule is formed on an electrode so as to measure a change in potential when the membrane adsorbs the aforementioned specific molecule. Specifically, the biosensor uses a system in which a membrane having glucose oxidase is formed on an electrode, and a change in current value caused by oxidation reaction with glucose is measured to detect the amount of glucose.

As for such biosensors, for example, refer to Japanese Patent Laid-Open No. 260156/1998; Aizawa, Chemical Communications, p.945 (1989); Alexander Star, Jean-Christophe P, Gabriel. Keith Bradley, and George Gruner, Vol. 3, No. 4, 459-463 (2003); etc.

The biosensors in the background art adopt a method for directly detecting a current value caused by chemical reaction as described above. Therefore, the detectability is so low that it is difficult to detect low-concentration glucose. In such a manner, the biosensors have a problem that they cannot show their own feature of high selectivity effectively.

An object of the present invention is to solve the foregoing problem in the background art and provide a single-electron transistor, a field-effect transistor, a sensor, a method for producing sensor, and a sensing method, having sensitivity much more excellent than that in the background art.

DISCLOSURE OF THE INVENTION

In order to attain the foregoing object, a first means of the present invention is a single-electron transistor including at least a substrate, a source electrode and a drain electrode formed on top of the substrate opposing to each other, and a channel arranged between the source electrode and the drain electrode, the single-electron transistor being characterized in that the channel is composed of ultra fine fibers.

A second means of the present invention is the first means characterized in that a gate electrode is formed in a site of the substrate other than the positions where the source electrode and the drain electrode are placed. For example, the gate electrode is provided in an opposite surface of the substrate to the surface where the source electrode and the drain electrode are placed, or in the same surface as the surface where the source electrode and the drain electrode are placed but in a position far from the source electrode and the drain electrode.

A third means of the present invention is the first means characterized in that a membrane having a functional group is provided on a surface of the substrate on the side where the channel is provided.

A fourth means of the present invention is the first or third means characterized in that an air gap is provided between a top surface of the substrate side and the channel.

A fifth means of the present invention is the first means characterized in that the ultra fine fibers are nanotube-like structures.

A six means of the present invention is the fifth means characterized in that the nanotube-like structures are carbon nanotubes.

A seventh means of the present invention is the fifth or sixth means characterized in that a defect is introduced into the nanotube-like structures.

An eighth means of the present invention is a field-effect transistor including at least a substrate, a source electrode and a drain electrode formed on top of the substrate opposing to each other, and a channel arranged between the source electrode and the drain electrode, the field-effect transistor being characterized in that the channel is composed of ultra fine fibers.

A ninth means of the present invention is the eighth means characterized in that a gate electrode is formed in a site of the substrate other than the positions where the source electrode and the drain electrode are placed.

A tenth means of the present invention is the eighth means characterized in that a membrane made of dielectric and having a functional group is provided on a surface of the substrate on the side where the channel is provided.

An eleventh means of the present invention is the eighth or tenth means characterized in that an air gap is provided between a top surface of the substrate side and the channel.

A twelfth means of the present invention is the eighth means characterized in that the ultra fine fibers are nanotube-like structures.

A thirteenth means of the present invention is the twelfth means characterized in that the nanotube-like structures are carbon nanotubes.

A fourteenth means of the present invention is the twelfth or thirteenth means characterized in that a defect is introduced into the nanotube-like structures.

A fifteenth means of the present invention is a sensor including at least a substrate, a source electrode and a drain electrode formed on top of the substrate opposing to each other, and a channel arranged between the source electrode and the drain electrode, the sensor being characterized in that the channel is composed of ultra fine fibers.

A sixteenth means of the present invention is the fifteenth means characterized in that a gate electrode is formed in a site of the substrate other than the positions where the source electrode and the drain electrode are placed.

A seventeenth means of the present invention is the sixteenth means characterized in that at least one electrode of the source electrode, the drain electrode and the gate electrode is composed of a titanium layer and a gold layer covering the surface of the titanium layer.

An eighteenth means of the present invention is the fifteenth means characterized in that a membrane having a functional group is provided on a surface of the substrate on the side where the channel is provided.

A nineteenth means of the present invention is the eighteenth means characterized in that the membrane is made of silicon oxide.

A twentieth means of the present invention is the fifteenth means characterized in that the ultra fine fibers are nanotube-like structures.

A twenty-first means of the present invention is the twentieth means characterized in that the nanotube-like structures are carbon nanotubes.

A twenty-second means of the present invention is the twentieth or twenty-first means characterized in that a defect is introduced into the nanotube-like structures.

A twenty-third means of the present invention is the fifteenth means characterized in that opposite end portions of the channel are welded with the source electrode and the drain electrode respectively.

A twenty-fourth means of the present invention is the fifteenth means characterized in that a surface of the channel is modified directly by a specific substance interacting with a substance to be detected.

A twenty-fifth means of the present invention is the fifteenth means characterized in that an insulating membrane is formed on a surface of the channel, and the insulating membrane is modified by a specific substance interacting with a substance to be detected.

A twenty-sixth means of the present invention is the sixteenth means characterized in that the gate electrode is modified by a specific substance interacting with a substance to be detected.

A twenty-seventh means of the present invention is any one of the twenty-fourth through twenty-sixth means characterized in that the substance to be detected and the specific substance are biopolymers interacting with each other.

A twenty-eighth means of the present invention is the twenty-seventh means characterized in that the substance to be detected is an antigen or an antibody, and the specific substance is an antibody or an antigen.

A twenty-ninth means of the present invention is the twenty-fourth means characterized in that portions which are not covered with a coat of the modifying substance are formed in a surface of the drain electrode and a surface of the gate electrode.

A thirtieth means of the present invention is a method for manufacturing a sensor including at least a substrate, a source electrode and a drain electrode formed on top of the substrate opposing to each other, and a channel arranged between the source electrode and the drain electrode, the method for manufacturing a sensor being characterized by providing catalysts in lines in the positions where the source electrode and the drain electrode are placed, opposing the two catalyst lines, and growing up ultra fine fibers from the source electrode to the drain electrode due to catalysis of the catalysts so as to arrange the channel.

A thirty-first means of the present invention is the thirtieth means characterized in that the catalysts are composed of a base layer, an intermediate layer made of a transition metal layer formed on the base layer, and a top layer made of a transition metal layer formed on the intermediate layer.

A thirty-second means of the present invention is the thirtieth or thirty-first means characterized in that the catalysts are patterned like dots so as to arrange the catalyst lines.

A thirty-third means of the present invention is the thirtieth means characterized in that the ultra fine fibers are nanotube-like structures.

A thirty-fourth means of the present invention is the thirty-third means characterized in that the nanotube-like structures are carbon nanotubes.

A thirty-fifth means of the present invention is the thirty-third or thirty-fourth means characterized in that a defect is introduced into the nanotube-like structures.

A thirty-sixth means of the present invention is a method for sensing a substance to be detected in a sample solution by means of a sensor including at least a substrate, a source electrode and a drain electrode formed on top of the substrate opposing to each other, and a channel arranged between the source electrode and the drain electrode, the sensing method being characterized in that the channel is composed of ultra fine fibers, the sample solution is dropped onto the channel, and a solvent of the sample solution is then evaporated.

A thirty-seventh means of the present invention is a method for sensing a substance to be detected in a sample solution by means of a sensor including at least a substrate, a source electrode and a drain electrode formed on top of the substrate opposing to each other, and a channel arranged between the source electrode and the drain electrode, the sensing method being characterized in that the channel is composed of ultra fine fibers, the sample solution is dropped onto the channel, and a solvent of the sample solution is then frozen.

A thirty-eighth means of the present invention is the thirty-sixth or thirty-seventh means characterized in that the ultra fine fibers are nanotube-like structures.

A thirty-ninth means of the present invention is the thirty-eighth means characterized in that the nanotube-like structures are carbon nanotubes.

A fortieth means of the present invention is the thirty-eighth or thirty-ninth means characterized in that a defect is introduced into the nanotube-like structures.

The present invention is configured as described above. Since ultra fine fibers such as carbon nanotubes are used for the channel, it is possible to provide a single electron transistor, a field-effect transistor, a sensor, a method for producing sensor, and a sensing method, which are supersensitive.

BEST MODE FOR CARRYING OUT THE INVENTION

Figure 1:
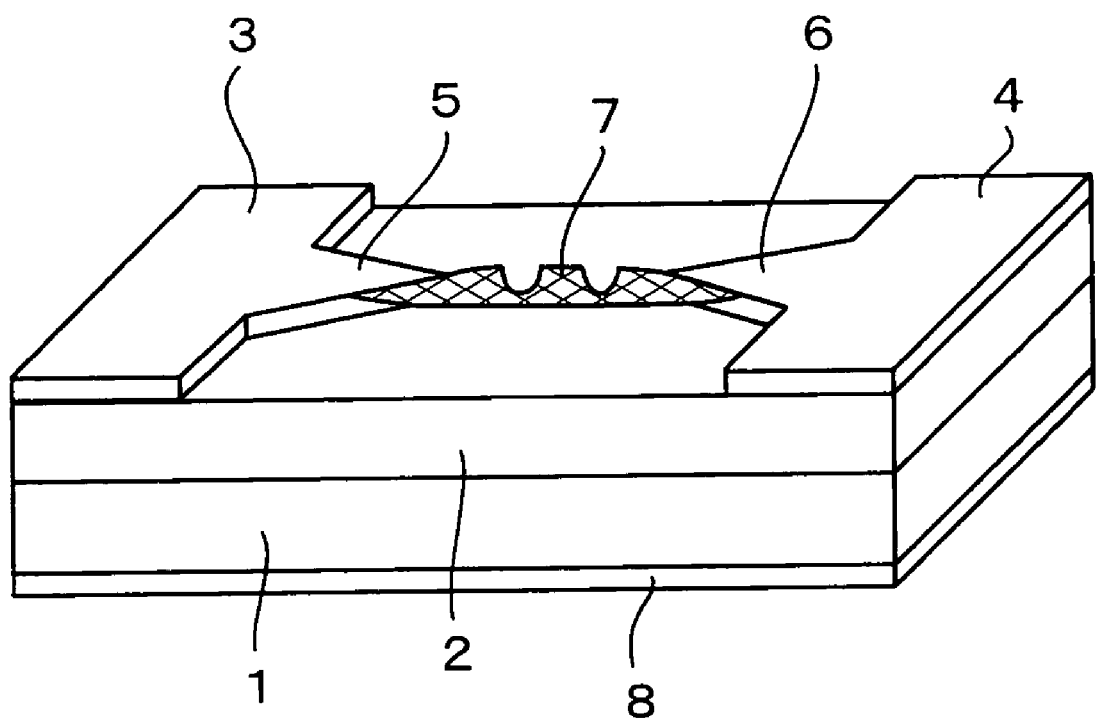
FIG. 1 is a perspective view of a sensor according to an embodiment of the present invention.
Figure 2:
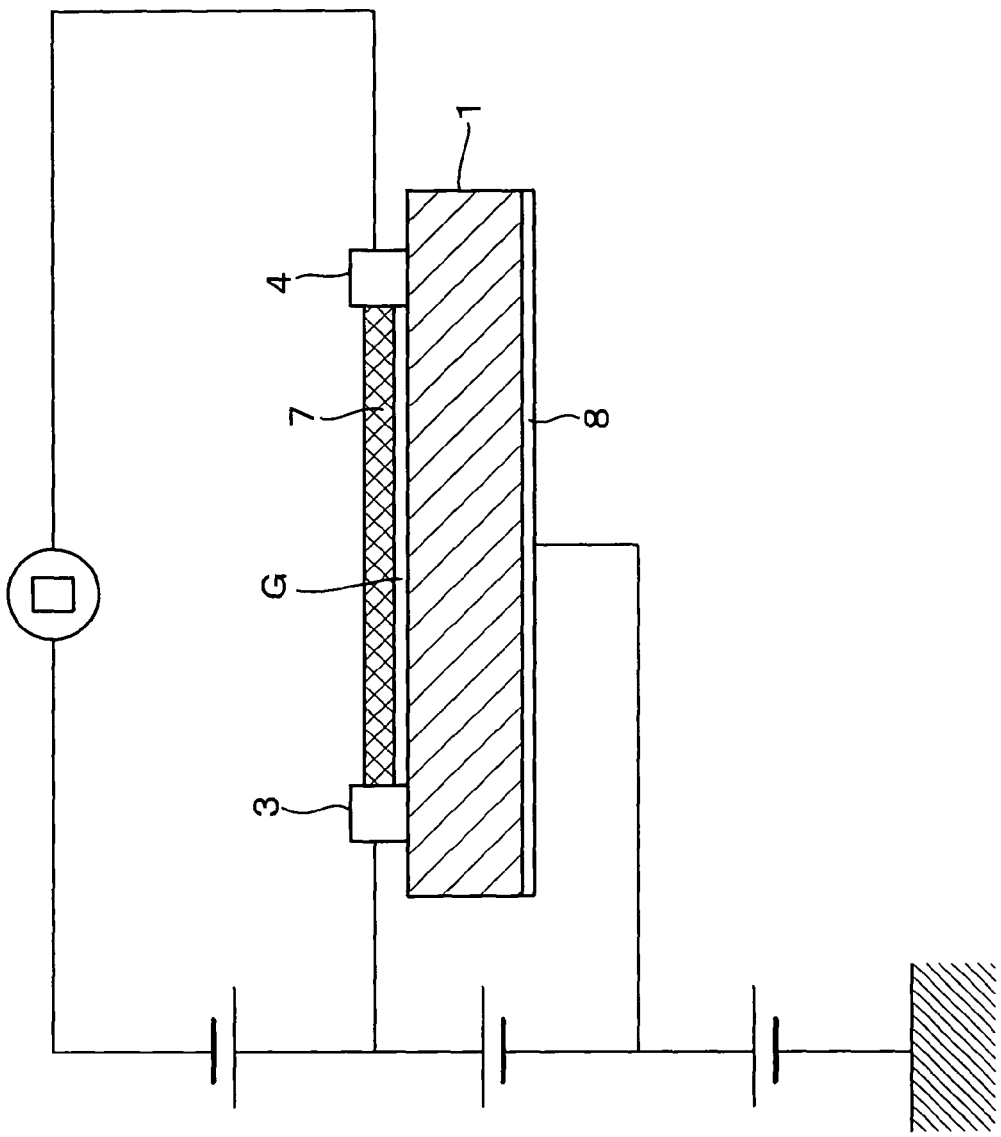
FIG. 2 is a schematic configuration view of the sensor.

Next, an embodiment of the present invention will be described with reference to the drawings. FIG. 1 is a perspective view of an SET type biosensor according to an embodiment of the present invention. FIG. 2 is a schematic configuration diagram of the SET type biosensor.

In these drawings, the reference numeral 1 represents a chip-like insulating substrate; 2, a membrane applied on the insulating substrate 1 and having a surface provided with a functional group such as a hydroxyl group, an amino group, a carboxylic group, etc. (membrane made of $SiO2$ with a hydroxyl group in this embodiment); and 3 and 4, a source electrode and a drain electrode formed at a predetermined interval on the membrane 2. Apical portions 5 and 6 are formed in opposed portions of the two electrodes 3 and 4 (see FIG. 1). Carbon nanotubes (hereinafter abbreviated to CNT) with a defect introduced therein are grown and formed between the apical portions 5 and 6 of the two electrodes 3 and 4. A gate electrode 8 is formed in a surface of the substrate 1 on the opposite side to the membrane 2.

Figure 8:
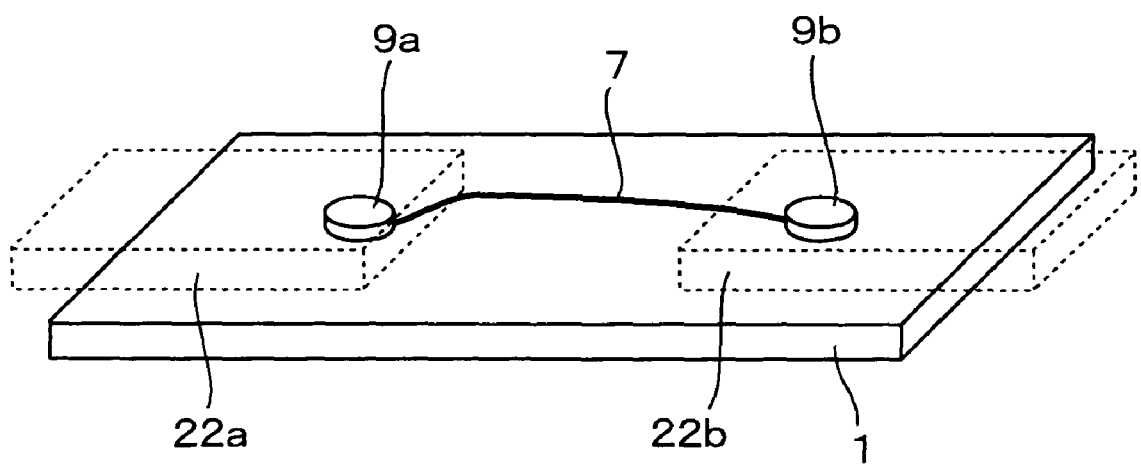
FIG. 8 is a schematic perspective view showing a state where a carbon nanotube is grown and formed by the background-art technique.

For example, an inorganic compound such as silicon oxide, silicon nitride, aluminum oxide, titanium oxide, etc. or an organic compound such as acrylic resin, polyimide, etc. is used for the insulating substrate 1. For example, metal such as gold, platinum, titanium, etc. is used for the electrodes 3, 4 and 8. The electrodes 3, 4 and 8 have an electric connection relationship as shown in FIG. 8.

CNTs are used as nanotube-like structures in this embodiment. Due to use of the nanotube-like structures, a very minute channel can be formed. Thus, a high sensitive sensor can be obtained.

Incidentally, as shown in FIG. 2, an air gap G is formed under the CNTs 7. A sensor having an SET structure is formed thus. SET and FET have the same fundamental structure, but are different from each other in a channel serving a current passageway. That is, a channel of SET has a quantum dot structure while a channel of FET does not have a quantum dot structure.

In this transistor (SET or FET), a current value between the source electrode 3 and the drain electrode 4 changes sensitively to a change of charges (more strictly spin electronic states) on the gate electrode 8 or the CNTs 7. SET is generally more sensitive than FET. However, SET properties are rare observed directly after CNTs are produced. When FET-like CNTs are heated to the temperature (high temperature of about 900° C.) in which the CNTs were produced, the CNTs are broken partially to form islands and show the current characteristic of SET. Alternatively, when a current (up to several mA) larger than an operating current (up to several $\mu A$) is applied, a similar result can be obtained.

According to the present invention, the spin electronic states on the CNTs change indirectly or directly when a molecule adheres to the gate electrode 8 or the CNTs 7 of the transistor. Thus, the adhering molecule can be detected from a change in current generated between the source electrode 3 and the drain electrode 4 in this event. A modifying molecule or a reaction between the modifying molecule and another molecule can be detected from a change in current when the gate electrode 8 or the CNTs 7 themselves are modified by the molecule.

Particularly when the gate electrode 8 or the CNTs 7 are modified by an antibody (or antigen), a specific antigen (or antibody) can be detected by use of antibody-antigen reaction. Accordingly, a microorganism such as a virus or a bacterium of infection can be detected supersensitively and fast in this technique. This technique can be effectively applied to early detection and prevention of infection or researches of microorganisms. In addition, a device (sensor) itself can be extremely miniaturized so that the device (sensor) can be brought out to the field and applied to detection of infectious viruses or researches of these.

Figure 3:
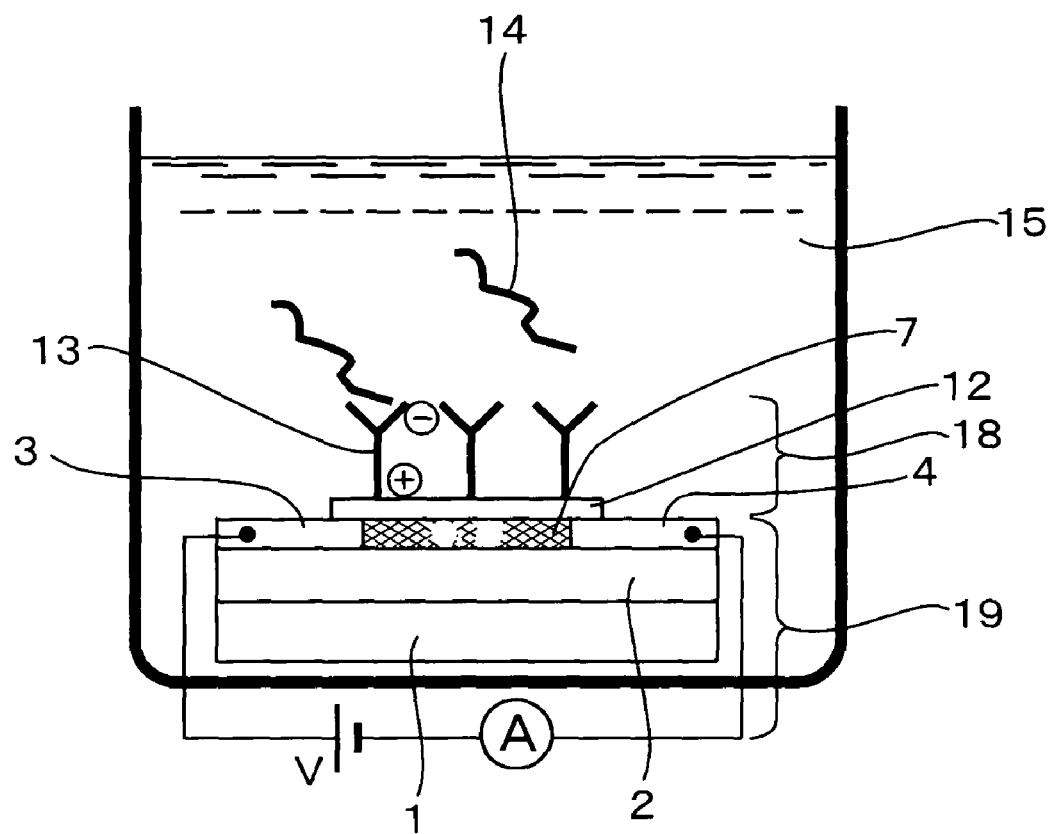
FIG. 3 is a schematic view showing a state where the sensor is applied to detection.

FIG. 3 is a schematic view showing the state where the sensor is applied to detection. As shown in FIG. 3, the sensor has a molecule detection portion 18 and a signal conversion portion 19 closely related to each other. In FIG. 3, the reference numeral 12 represents a protective film made of SiO2; 13, a specific substance (e.g. antibody) selectively reacting or sticking (interacting) to a substance to be detected; 14, a to-be-detected substance (e.g. antigen) selectively reacting or sticking (interacting) to the specific substance 13; and 15, a sample solution containing the to-be-detected substance 14.

Figure 4:
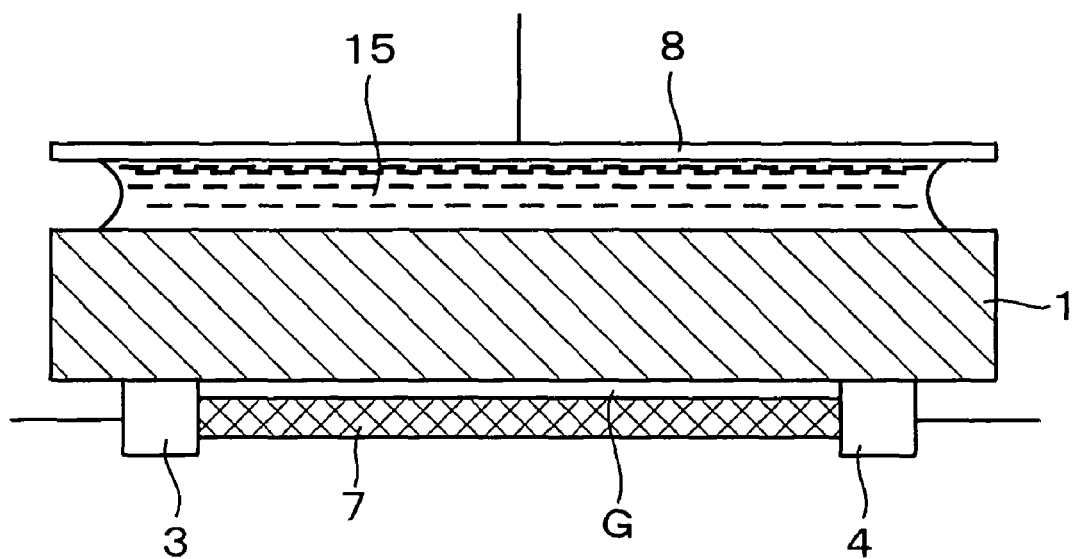
FIG. 4 is a schematic view showing another state where the sensor according to the embodiment of the present invention is applied to detection.
Figure 5:
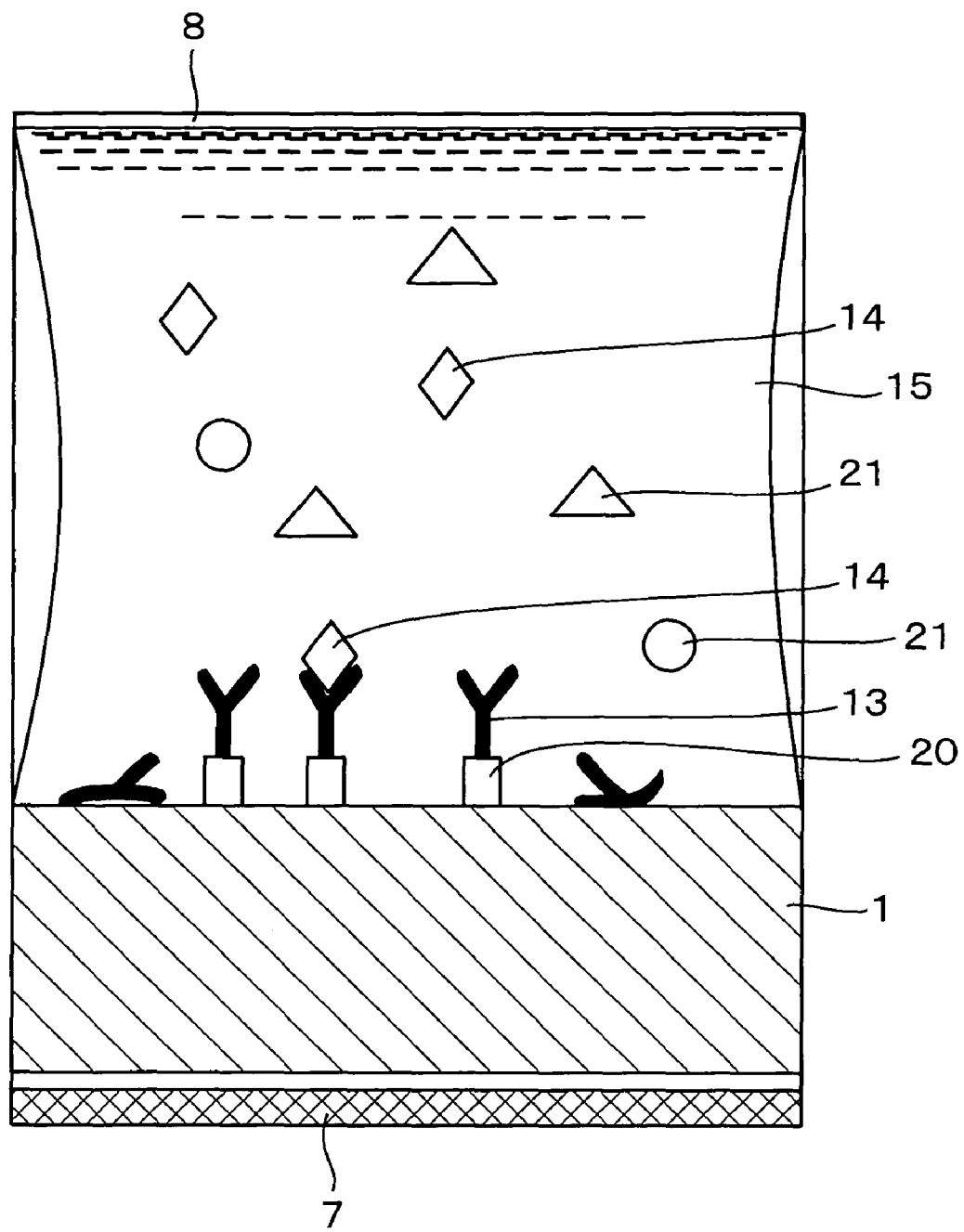
FIG. 5 is an enlarged schematic view of the sensor between an insulating substrate and a gate electrode.

FIG. 4 and FIG. 5 are schematic views showing another state where the sensor according to the present invention is applied to detection. FIG. 5 is a schematic enlarged view of the sensor between the insulating substrate 1 and the gate electrode 8. In the case of this example, the sample solution 15 containing the to-be-detected substance 14 is put between the insulating substrate 1 and the gate electrode 8 so as to detect the to-be-detected substance 14. In FIG. 5, the reference numeral 20 represents a molecule of the specific substance (e.g. antibody) having an orientation; and 21, a substance other than the to-be-detected substance present in the sample solution 15. FIG. 5 shows the state where the specific substance (e.g. antibody) 13 selectively reacts or sticks to the to-be-detected substance (e.g. antigen) 14.

Next, description will be made on control of the fundamental electric transport properties of the CNTs.

(1) The application of an electric field or a magnetic field, the kind and shape of a catalyst to be used for growing up the CNTs, and so on, are optimized to desirably design the growth position, direction, number, chirality, properties, etc. of the CNTs serving as a base element of the biosensor device.

Figure 6:
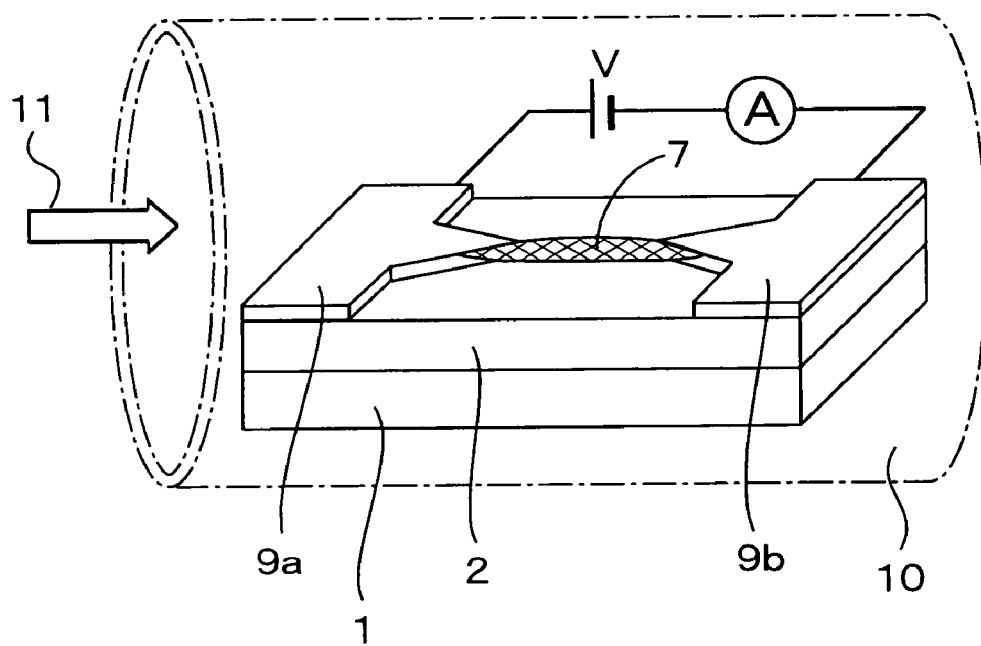
FIG. 6 is a schematic configuration view showing a state where carbon nanotubes are grown and formed in the embodiment of the present invention.

FIG. 6 is a schematic configuration view showing a technique for patterning the catalyst and controlling the position and direction of CNTs while applying an electric field thereto. In FIG. 6, the reference numeral 1 represents an insulating substrate; 2, a membrane made of SiO2 applied onto the insulating substrate 1; 9a and 9b, catalyst layers patterned on the SiO2 membrane 2 and made of iron or the like; 7, CNTs formed between the catalyst layers 9a and 9b by application of the electric field. The growth position, direction, number, chirality, properties, etc. of the CNTs 7 are controlled desirably. The reference numeral 10 represents a reaction chamber; and 11, hydrocarbon gas such as methane gas or the like, which is a raw material of the CNTs. The grown CNTs are formed into an ultrafine fibrous aggregate measuring about several μm (e.g. about 3 μm) in length and about several nm in diameter.

(2) The CNTs whose position, direction, properties, etc. have been controlled are used as a noninvasive electrode to make up a shape of a four-probe method.

The four-probe method is a method using four needle-like electrodes (e.g. electrodes A, B, C and D) placed in a straight line on a specimen. A constant current is applied between the outer two (e.g. electrodes A and D) of the probes. A potential difference appearing between the inner two (e.g. electrodes B and C) of the probes is measured to obtain a resistance value. The obtained resistance value is multiplied by the thickness of the specimen and a correction coefficient RCF. Thus, a volume resistance value of the specimen is calculated.

(3) Each electrode and the channel (CNTs) are welded in their lapping portion by a locally impressed current using a high-electric-field electron beam, or STM (Scanning Tunneling Microscopy)/AFM (Atomic Force Microscope). Thus, the electrodes and the channel (CNTs) are integrated.

(4) Next, the transport properties of the CNTs are evaluated. Electric transport properties to be evaluated include the ballistic transport properties, the spin injection probability, the spin transport probability, etc.

(5) By pilot studies of the present inventors, it has been confirmed that the electric properties of the CNTs change on a large scale due to a defect introduced into the CNTs (it has been confirmed by the pilot studies that Coulomb energy up to 5,000 K is provided due to a defect introduced into the CNTs, so that SET acting in a room temperature can be formed).

Accordingly, when a defect is desirably introduced into the CNTs by STM/AFM processing or by an electron beam, CNTs having controllable electric transport properties can be obtained.

As a specific example of the method for introducing a defect into the CNTs, there is a method in which the CNTs are, for example, annealed at almost the same temperature (e.g. about 800° C.) as the CNTs were produced, and then cooled naturally. The defect of the CNTs means that a part of carbon atoms fly out due to heat, with the result that the CNTs are changed in shape or the like so that the CNTs are nearly broken into pieces narrowly connected to one another. However, it is not obvious as of now what structure the CNTs have actually.

(6) The correlation between the defect in the CNTs and the electric properties of the CNTs is investigated. For example, the density, distribution and magnitude (size, energy barrier, etc.) of the defect are evaluated by a scanning probe method (a Kelvin probe method, a Maxwell probe method, etc.) so as to clarify the correlation between the defect and the electric properties of the CNTs. When the correlation between the defect in the CNTs and the electric properties of the CNTS is grasped thus, it is possible to manufacture SET having properties excellent in reproducibility and uniformity.

(7) The electric properties of the carbon nanotubes can be controlled by controlling the introduction of the defect in the aforementioned process (6).

SET acting in a room temperature can be manufactured using the CNTs having a defect introduced therein according to the present invention. Here, description has been made on the case where the CNTs having a defect introduced therein are used. However, CNTs having no defect introduced therein may be used.

Floating charges or moving charges have leaded to problems in SET in the background art. In order to avoid malfunction caused by such floating charges or moving charges, according to the present invention, two SETs using CNTs are produced to be close to each other, and the output characteristics (room temperature) of the two SETs are ANDed when a single charge is detected. As a result, the two SETs operate only when there is a true charge. Thus, malfunction caused by floating charges or moving charges can be avoided.

Further, not a background-art DC system but an AC drive system using a resonance circuit by use of the aforementioned technique is used to increase the measurement speed. Thus, a single charge distribution can be measured at a room temperature, at a high speed and without malfunction.

Figure 7:
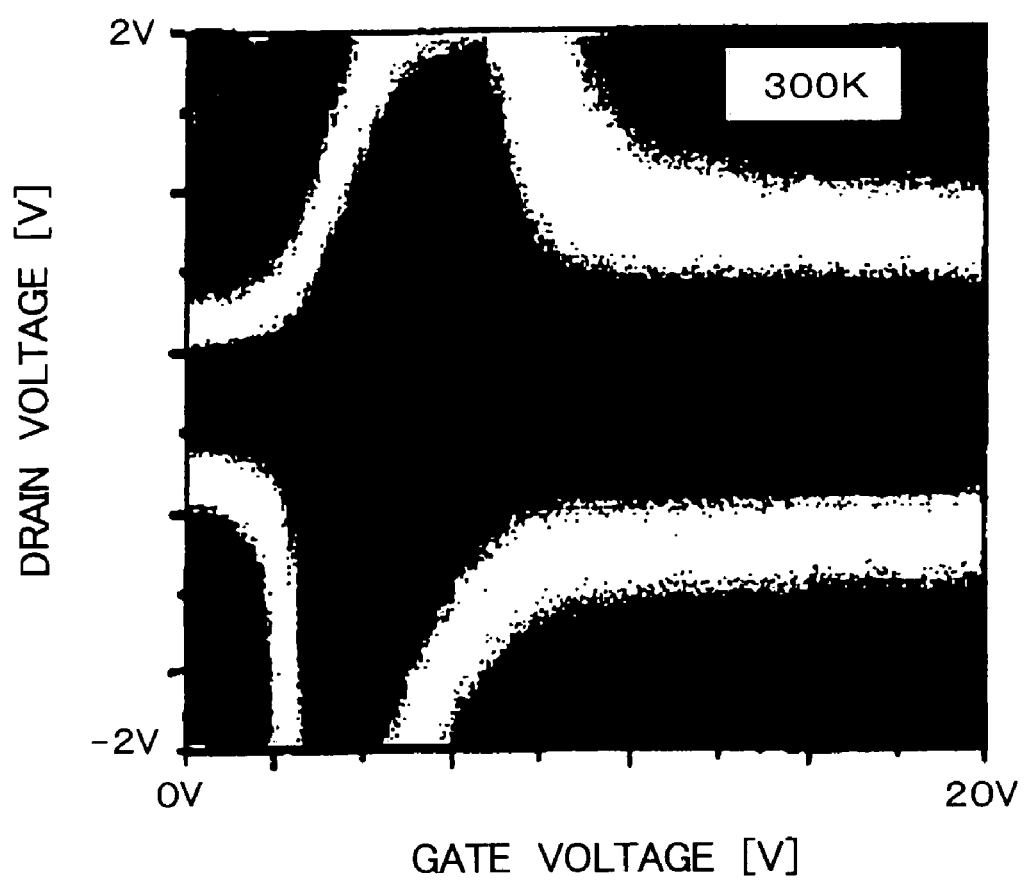
FIG. 7 is a view showing a room temperature Coulomb diamond characteristics with a carbon-nanotube single-electron transistor.

FIG. 7 is a view showing room temperature Coulomb diamond characteristics with SET using CNTs. From the room temperature Coulomb diamond characteristics, it can be proved that the SET using CNTs according to the present invention can operate at a room temperature.

As shown in FIG. 1, SET using CNTs is formed on the substrate 1, while the chip is coated with the protective film 12 made of SiO2 in order to be operated in a solution as shown in FIG. 3, and the specific substance 13 such as an antibody is fixed onto the SiO2 protective film 12. Although the protective film 12 is provided in this embodiment, there may be a case where the protective film 12 does not have to be provided.

The biosensor according to this embodiment is installed in the sample solution 15 in which the to-be-detected substance 14 such as DNA or the like has been dissolved. The biosensor is operated by AC using a resonance circuit, so as to measure a single electron interaction between the specific substance 13 and the to-be-detected substance 14. Thus, the to-be-detected substance 14 can be detected (surface charge distribution characteristics can be evaluated).

Next, description will be made in detail on production of the signal conversion portion of the sensor using CNTs. An FET or SET type transistor is produced using the semiconductor properties of CNT. The production method is constituted by the processes of depositing catalysts by general lithography, growing CNT by thermal CVD, and producing electrodes.

However, this has problems as follows. First, it is not easy to control the growth of CNT. Some CNT growing methods have been proposed. When a device in which electrodes in a signal conversion portion are connected through a single CNT is formed, yield and structural stability of the CNT bridging catalysts are important. Therefore, conditioning of the catalysts (mutual positions, structures, sizes, etc.) and conditioning of the thermal CVD method (temperature, kind of gas, flow rate, introduction of electric field or magnetic field, etc.) are important.

Further, the electrodes are produced after the growth of the CNT on the catalysts. However, it is likely that there appears such a phenomenon that the electrodes are separated from the substrate or the electrodes are cracked. It is also likely that the contact potential with the CNT affects the characteristic or strength of the device. In order to obtain a stable current characteristic, it is necessary to investigate the electrode materials.

In the embodiment of the present invention, a novel technique (first technique which will be described later) is used particularly for elements of the catalysts. When CNT is modified directly by a molecule, the electrodes may be covered with a solvent including the electrodes and the molecule so that the solvent covering the surfaces of the electrodes may affect the connection between the electrodes and a measuring device such as a prober. Therefore, a technique (second technique which will be described later) for preventing this is used.

Further, even when a back gate electrode or a side gate electrode is used in the device, a specimen, vapor containing the specimen, or the like, may affect the gate electrode. This can be avoided by protecting the CNT (third technique which will be described later). In fact, of results of detection of reactions using a back gate electrode or a side gate electrode, there was an example in which it could be believed that a change in current value was caused by a to-be-detected substance evaporated and attached to not only the gate electrode but also the surface of CNT.

Specifically, the aforementioned first technique is to deposit catalysts onto an SiO2 film by use of electron-beam lithography in order to form nuclei of growth of CNTs. In this embodiment, the first technique relates to a technique in which each of the opposite surfaces of an Si substrate 380 μm thick is covered with an SiO2 film about 300 nm, and catalysts containing transition metal such as iron, nickel, cobalt, molybdenum, tungsten, etc. or particles of such a transition metal are deposited on the SiO2 film as nuclei of growth of CNTs.

FIG. 8 is a view for explaining a background-art technique. In FIG. 8, the reference numeral 1 represents an Si insulating substrate having an SiO2 film formed on each of the opposite surfaces thereof; 7, a CNT; 9a and 9b, catalysts; and 22a and 22b, positions where electrodes will be formed later. In the background-art technique, as shown in FIG. 8, the catalysts 9a and 9b are formed at a predetermined interval one by one by vapor deposition so that the catalysts 9a and 9b can be connected by the CNT 7 as soon as the CNT 7 grown from one catalyst 9a reaches the paired catalyst 9b.

Figure 9:
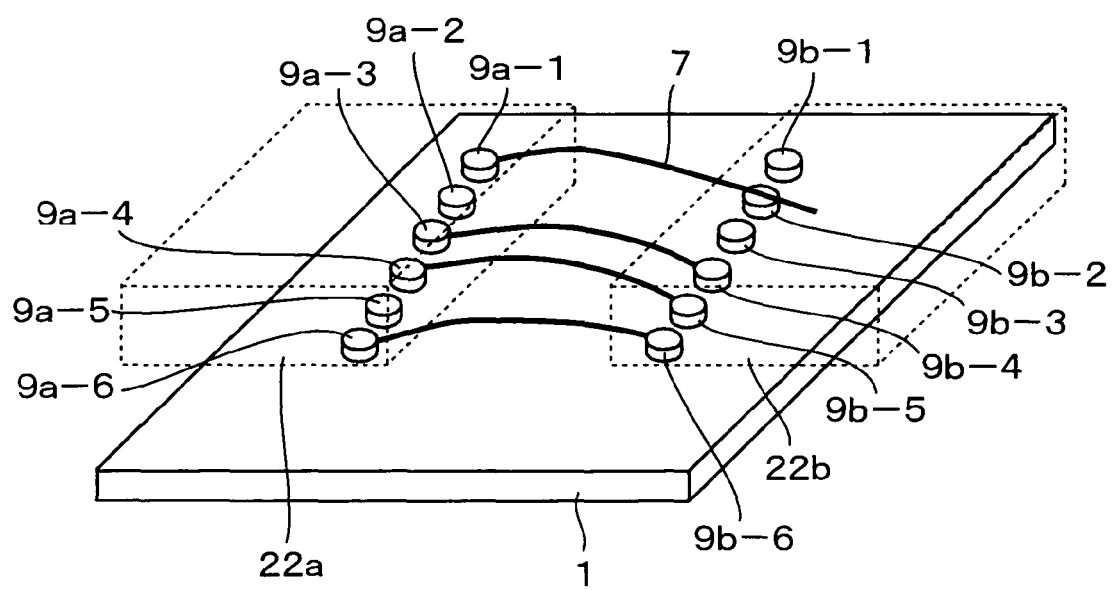
FIG. 9 is a schematic perspective view showing a state where carbon nanotubes are grown and formed by the technique of the present invention.

FIG. 9 is a view for explaining the embodiment (first technique) of the present invention. As shown in FIG. 9, a plurality of dot-like catalysts (9a-1, 9a-2, . . . 9a-n) are formed and arranged in a position 22a where one electrode will be formed, and a plurality of dot-like catalysts (9b-1, 9b-2, . . . 9b-n) are also formed in a position 22b where the other electrode will be formed, so that the catalysts (9b-1, 9b-2, . . . 9b-n) are opposed to the aforementioned catalysts (9a-1, 9a-2, . . . 9a-n). In such a manner, the number of the catalysts 9 placed, that is, the number of nuclei of growth of CNTs is increased so that the catalysts 9 are arrayed thickly. Thus, it is possible to extremely increase the probability that the CNTs easy to grow up at random from the catalysts 9 in themselves will reach the paired catalysts 9. Due to this technique, the yield can be made 10 or more times as high as that in the background art.

Figure 10:
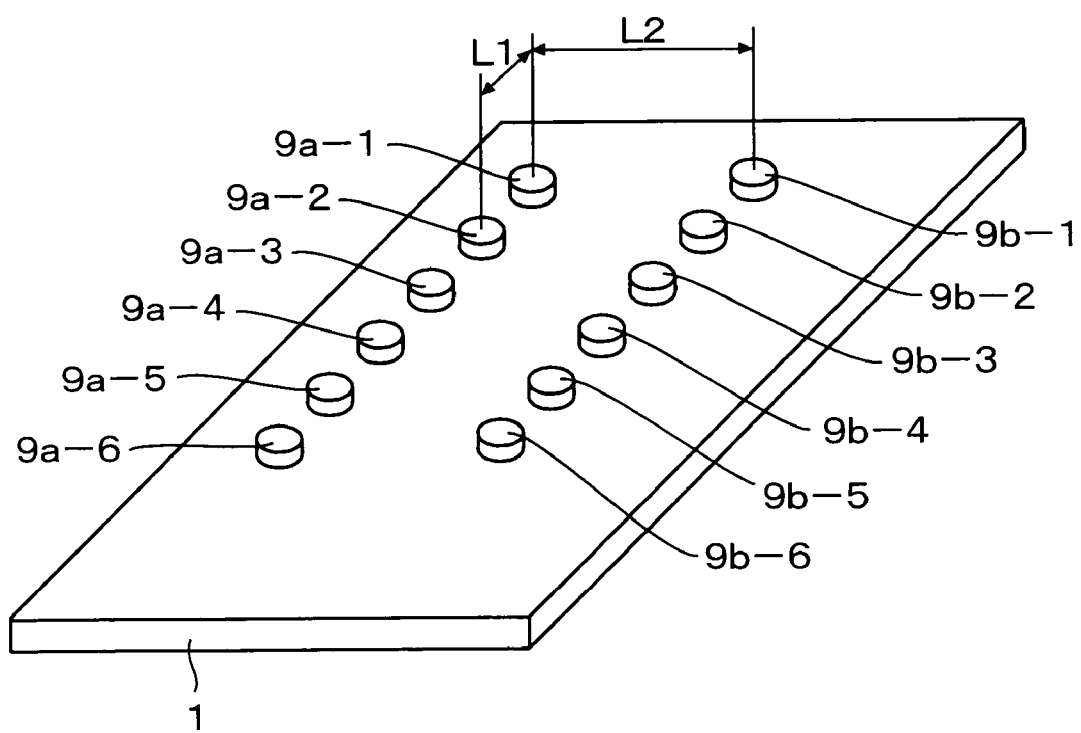
FIG. 10 is a schematic perspective view showing an example of the layout of catalysts according to the technique of the present invention.

FIG. 10 is a view showing an example of the layout of the catalysts 9 according to this embodiment. Six catalysts are arranged thickly in each array so that an interval L1 between adjacent catalysts is 2 μm. An interval L2 between one catalyst array (9a-1, 9a-2, . . . 9a-n) and the other catalyst array (9b-1, 9b-2, . . . 9b-n) is 4 μm. Incidentally, the number of the catalysts 9 placed, the interval L1 and the interval L2 can be set desirably.

Figure 11:
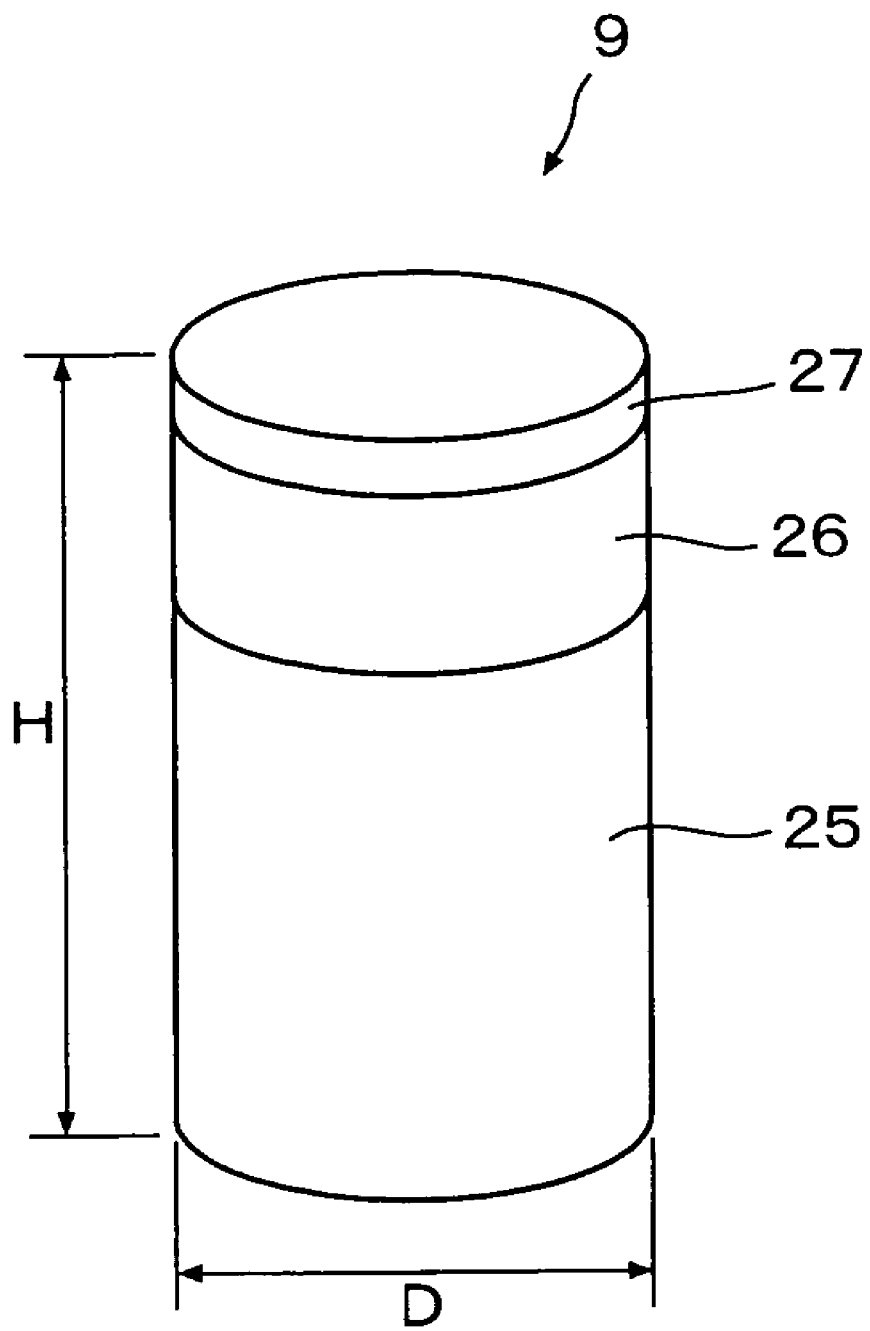
FIG. 11 is an enlarged perspective view of the catalyst.

FIG. 11 is an enlarged perspective view of the catalyst 9. As shown in FIG. 11, the catalyst 9 has a three-layer structure of a base layer 25, an intermediate layer 26 and a top layer 27. The base layer 25 is made of Si or the like and has a thickness of 50 nm. The intermediate layer 26 is formed on the base layer 25, made of transition metal such as Mo, Ta, W, etc. and has a thickness of 10 nm. The top layer 27 is formed on the intermediate layer 26, made of transition metal such as Fe, Ni, Co, etc. and has a thickness of 3 nm. Accordingly, the total height of the catalyst 9 is 63 nm, and the diameter D thereof is 2 μm. The catalysts 9 each having such a multilayer structure are patterned by a thin film formation technique such as vapor deposition, sputtering, ion plating, etc.

The insulating substrate 1 where the catalysts 9 have been formed is placed in a reaction chamber 10 of a thermal CVD apparatus as shown in FIG. 6. After that, hydrocarbon gas 11 such as methane, ethane or the like is injected to grown the CNTs 7 on the catalysts 9.

In this embodiment, the growth of the CNTs 7 is performed in the following procedure. The insulating substrate 1 where the catalysts 9 have been formed is heated from the room temperature to 900° C. for 15 minutes. In this event, Ar is injected into the chamber 10 at a flow rate of 1,000 sccm (gas flow rate per minute). Methane and hydrogen are injected at flow rates of 1, 000 sccm and 500 sccm respectively for 10 minutes while keeping the temperature. After that, the inside of the reaction chamber 10 is cooled down to the room temperature for 120 minutes. In this event again, Ar gas is injected at 1,000 sccm.

After the CNTs are produced thus, electrodes (source electrode 3 and drain electrode 4) are deposited. Au is deposited on the electrodes. Alternatively, Ti is deposited on the electrodes, and the surfaces thereof are then coated with Au.

Particularly the latter method is characterized in that it can suppress the separation of the electrodes from the substrate or the occurrence of cracks in the electrodes. The width of the electrodes covering the catalysts is about 10 μm.

Next, description will be made on the aforementioned second technique. A large number of electrodes (about 50-400 electrodes) are formed concurrently. For example, when CNT is modified directly, a solution containing a modifying molecule may be dropped down onto the CNT. In this event, the solution may cover the whole of an electrode depending on some amount of the solution. Once the surface of the electrode is covered with the solution, a coat may be formed between a probe of a measuring device such as a prober and the electrode when a current between electrodes connected by the CNT is measured. Thus, it is likely that a correct current value cannot be obtained.

Figure 12:
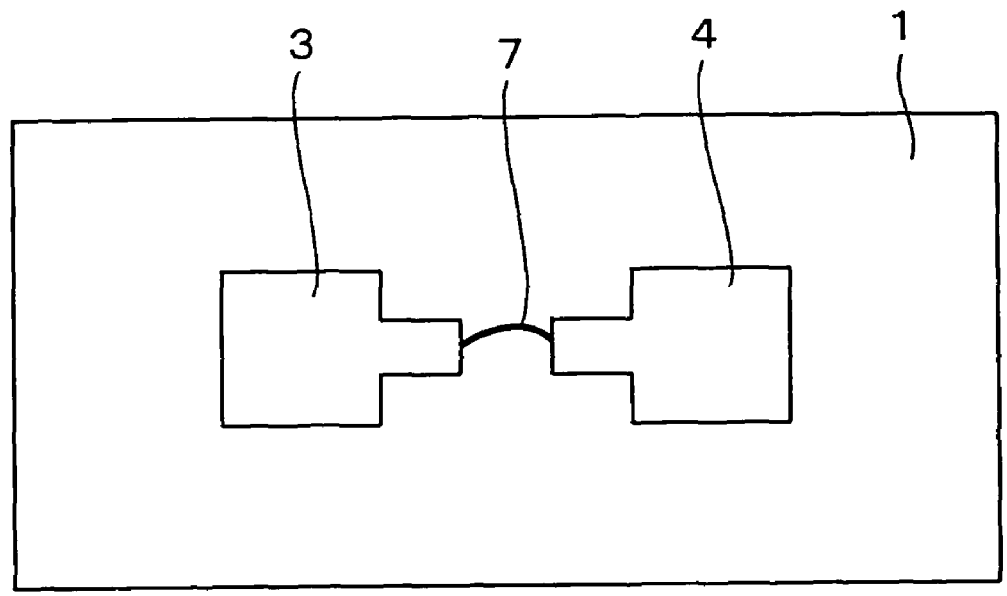
FIGS. 12 are a plan view (a) and a sectional view (b) of a sensor to which a second technique is not applied.
Figure 12:
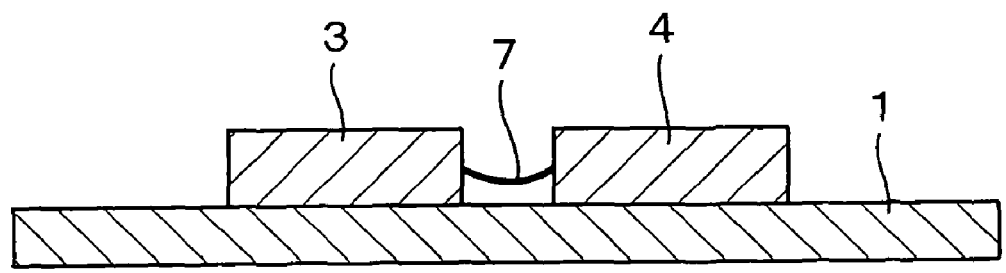
Figure 13:
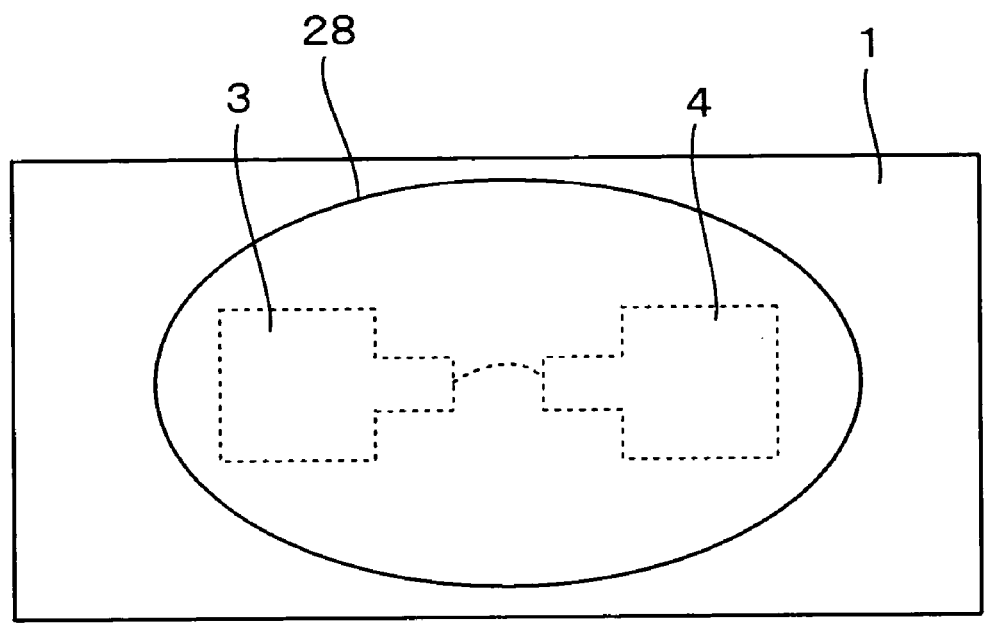
FIGS. 13 are a plan view (a) and a sectional view (b) of the sensor showing a state where a solution has been dropped onto the sensor.
Figure 13:
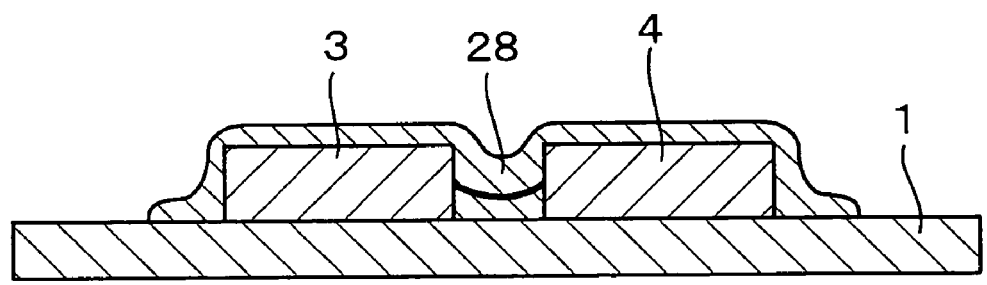

FIGS. 12 and FIGS. 13 are views for explaining a sensor to which the second technique is not applied. FIGS. 12 are views showing a state before a solution is dropped. FIGS. 13 are views showing a state after the solution is dropped. In FIGS. 12 and 13, (a) shows a plan view, and (b) shows a sectional view. The electrodes 3 and 4 are small in size in the background-art sensor. Therefore, the electrode 3, 4 is often entirely covered with a coat 28 formed by the solution dropped, as shown in FIGS. 13. A value of a current flowing between the electrodes 3 and 4 is about 1 μA, which is so minute that the current cannot be measured correctly if the coat 28 is present between the probe of the measuring apparatus and the electrode 3, 4.

Figure 14:
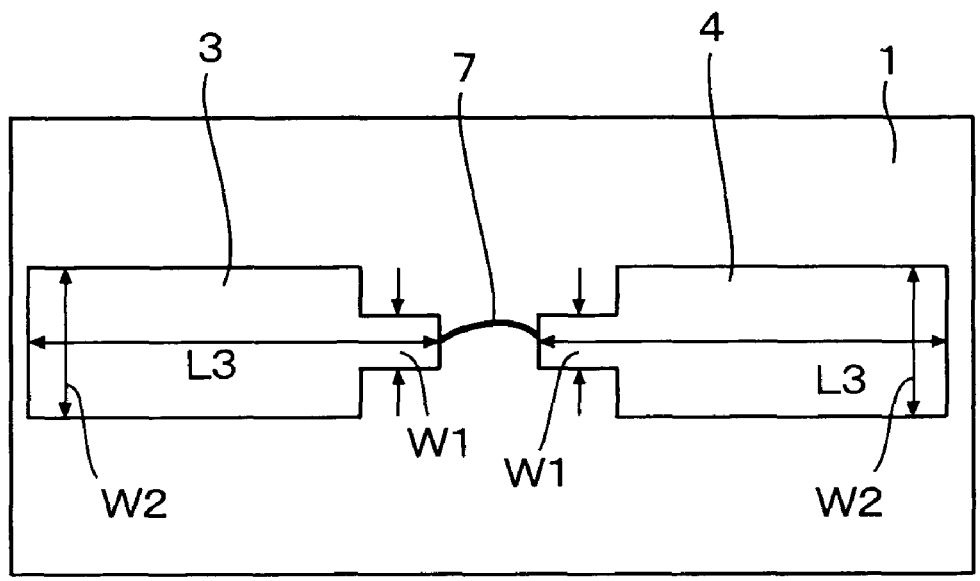
FIGS. 14 are a plan view (a) and a sectional view (b) of the sensor according to the present invention.
Figure 14:
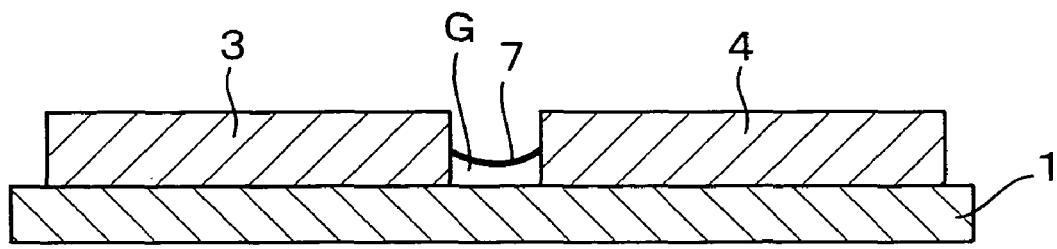
Figure 15:
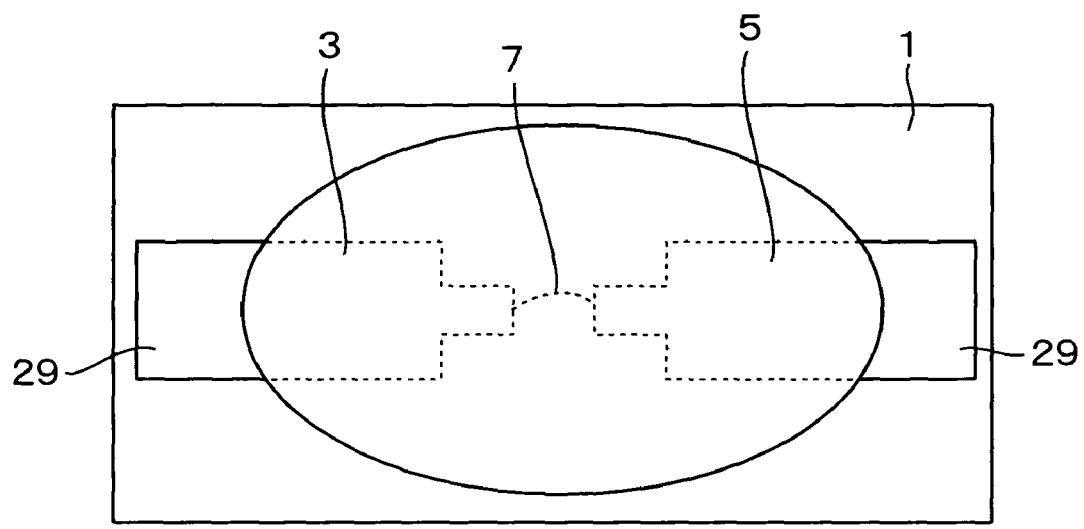
FIGS. 15 are a plan view (a) and a sectional view (b) of the sensor showing a state where a solution has been dropped onto the sensor.
Figure 15:
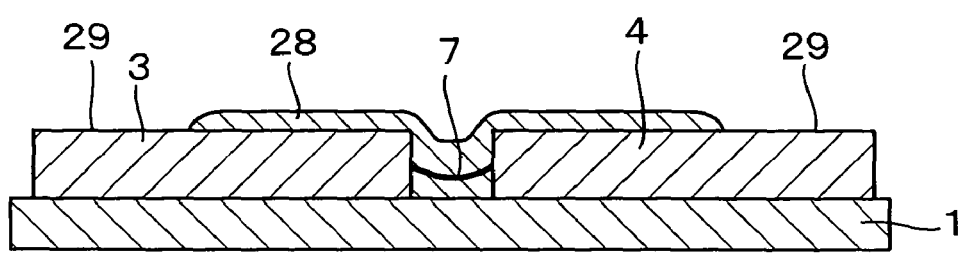

Therefore, according to the present invention, as shown in FIGS. 14 and FIGS. 15, length L3 of each electrode 3, 4 [see FIG. 14(a)] is made about 1.5-3 times as long as that in FIGS. 12. Thus, since length L3 of the electrode 3, 4 is made longer thus, a portion 29 (see FIGS. 15) which is not covered with the coat 28 can be formed in an end portion of the electrode 3, 4 even if the coat 28 of the molecule modifying the CNTs 7 is formed. By use of an optical microscope, the probe of the measuring apparatus such as a prober is applied to this portion 29 which is not covered with the coat 28. Thus, the current flowing between the electrodes 3 and 4 can be measured correctly.

In this embodiment, width w1 of the tip portion, width W2 of the portion the probe will be applied to, and length L3 are made 10 μm, 150 μm and 500 μm respectively in each electrode 3, 4 in FIG. 14(a). As shown in FIG. 14(b), the CNTs 7 are slightly bent between the electrodes 3 and 4 so that an air gap G is provided between the CNTs 7 and the top surface of the substrate 1 side. Thus, the difference in thermal expansion coefficient from the substrate 1 is absorbed by the slack of the CNTs 7.

Next, description will be made on the aforementioned third technique. It is said that CNT has strength 2,000 times as high as iron when they have same size. In fact, CNT is hardly damaged when the CNT is cleansed after the CNT is modified directly by a molecule. However, CNT easily interacts with various molecules including water so as to change its spin electronic states. The change appears as a change in current value. This can be positively used as a gas sensor. At the same time, when a back gate electrode, a side gate electrode, or the like, is used in a sensor, CNT may be a noise source.

Therefore, according to the present invention, the CNTs and the electrodes are partially covered with an insulating protective film so as to reduce the noise. An insulating adhesive agent can be used for forming the insulating film. A passivation film used broadly for spin coating can be also used. Particularly the increase of a current which would appear when water was given to the back gate electrode is not observed due to the formation of the insulating protective film. In addition, due to the formation of this insulating protective film, ultrasonic cleaning can be applied to the device as a whole, or the back gate electrode and so on can be cleansed with detergent more powerful than ever.

The gate electrode of the sensor can be formed in various positions. The gate electrode can have various structures in accordance with the application of the sensor or the easiness to manufacture the sensor. Next, description will be made on each structure.

(A) Structure of Gate Electrode Modified by Molecule

When a molecule adheres onto the SiO2 film formed on the substrate, there appears a change in value of the current flowing between the source electrode and the drain electrode. For example, the current value changes when a fluorescent molecule FITC (Fluoresceinisothiocyanate) is given to the gate electrode. As an example of antibody-antigen reaction, the SiO2 film is molecule-modified by an antibody (or antigen) so as to react to a corresponding antigen (or antibody) and detect a change in electric signal. Molecule modification can be attained in a larger area than that in CNT. Thus, this molecule modification is suitable for detection aimed at more molecules. In addition, since CNT is not modified directly, damage of the CNT caused by cleaning after use can be avoided.

Figure 16:
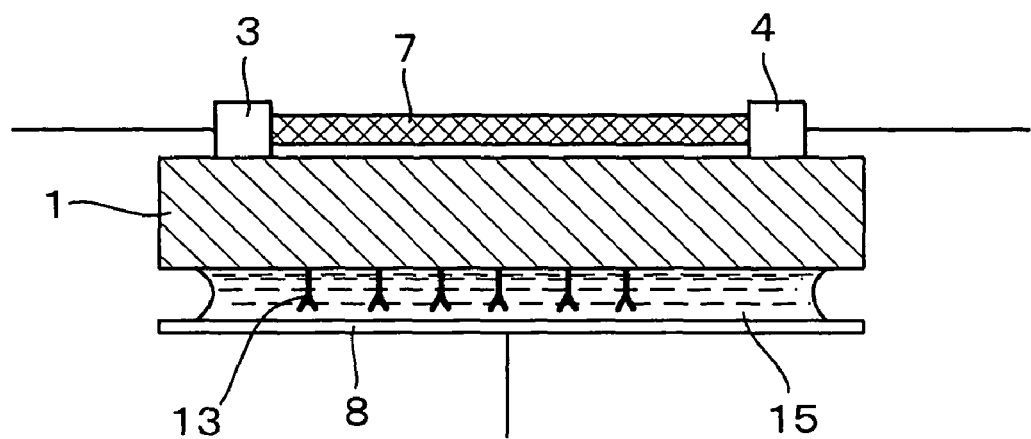
FIG. 16 is a sectional view showing a state where a back gate electrode is modified in the sensor according to the present invention.

FIG. 16 is a view showing this structure. In this structure, as shown in FIG. 16, the SiO2 film on the insulating substrate 1 on the opposite side to the CNTs 7 is molecule-modified by a specific substance (e.g. antibody) 13, while a sample solution 15 containing a to-be-detected substance (e.g. antigen) is put between the insulating substrate 1 and the gate electrode 8.

(B) Structure of CNTs Modified Directly by Molecule

Figure 17:
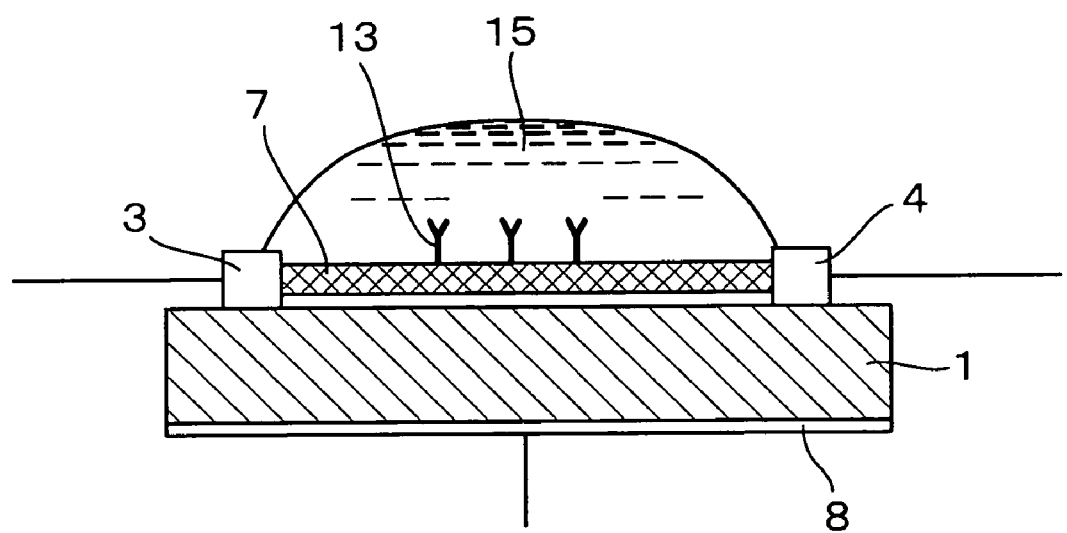
FIG. 17 is a sectional view showing a state where carbon nanotubes are modified directly by a molecule in the sensor according to the present invention.

FIG. 17 is a view showing a structure in which the CNTs 7 are modified directly by a molecule. Since the CNTs 7 are modified directly by a molecule, a change in spin electronic states on the CNTs 7 caused by the modifying molecule is larger than that in the case where the back gate electrode 8 is modified by a molecule. Thus, high sensitivity is provided.

(C) Structure of CNTs Modified Indirectly by Molecule

Figure 18:
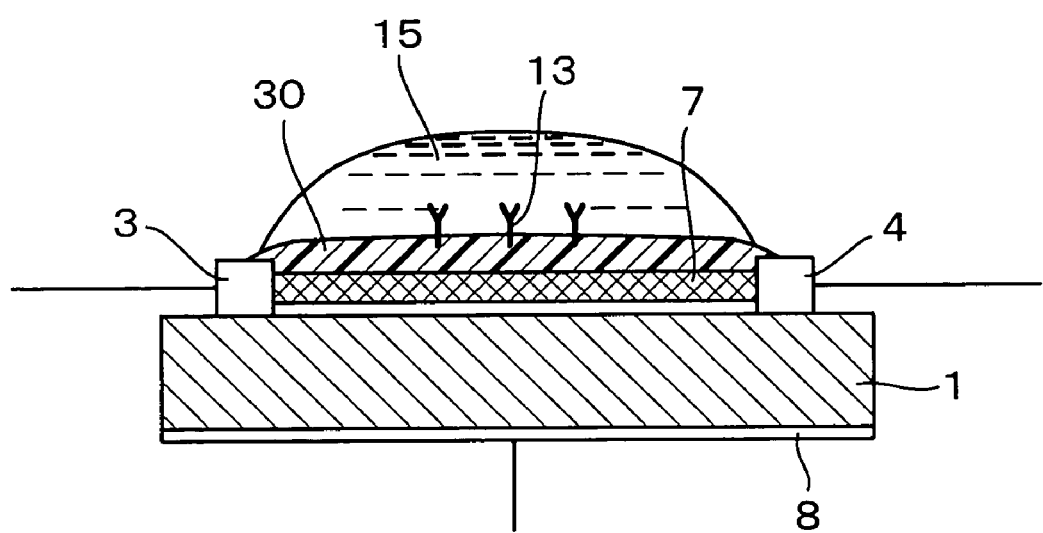
FIG. 18 is a sectional view showing a state where the carbon nanotubes are modified indirectly by a molecule in the sensor according to the present invention.

FIG. 18 is a view showing a structure of the CNTs 7 modified indirectly by a molecule. In order to modify the CNTs 7 indirectly by a molecule, the CNTs 7 are coated with an insulating membrane 30 made of an organic compound such as an adhesive agent or the like as shown in FIG. 18. A change in spin electronic states in the membrane 30 caused by the modifying molecule or a molecule adhering thereto leads to a change in spin electronic states in the CNTs 7. As a result, there occurs a change in current. This structure has both the feature as the structure in which the back gate electrode 8 is modified by a molecule and the feature as the structure in which the CNTs 7 are modified directly by a molecule. Thus, the structure has high sensitivity and stability.

(D) Structure Using Sol-Gel

In each of the aforementioned structures (A) to (C), sol-gel containing a to-be-detected substance is used in place of the solution 15. A change in electric signal can be detected in the same manner as in the case of the solution.

(E) Structure Using Side Gate

An island is built near the CNTs on the substrate, and this is used as a gate. This structure is characterized in that the CNTs 7 themselves can be prevented from being damaged by direct modification of the CNTs 7 without any effort such as modification of the back surface (back gate electrode) by a molecule. Thus, this is a structure suitable for SET.

In the aforementioned structure (A) of the back gate electrode modified by a molecule, it is preferable that the CNTs and the electrodes are partially covered with a protective film so as to stabilize the current characteristic. In the aforementioned structure (B) of the CNTs modified directly by a molecule and in the aforementioned structure (C) of the CNTs modified indirectly by a molecule, it is preferable that a portion 29 which is not covered with a coat is formed on each electrode 3, 4 as described with reference to FIGS. 15.

Figure 19:
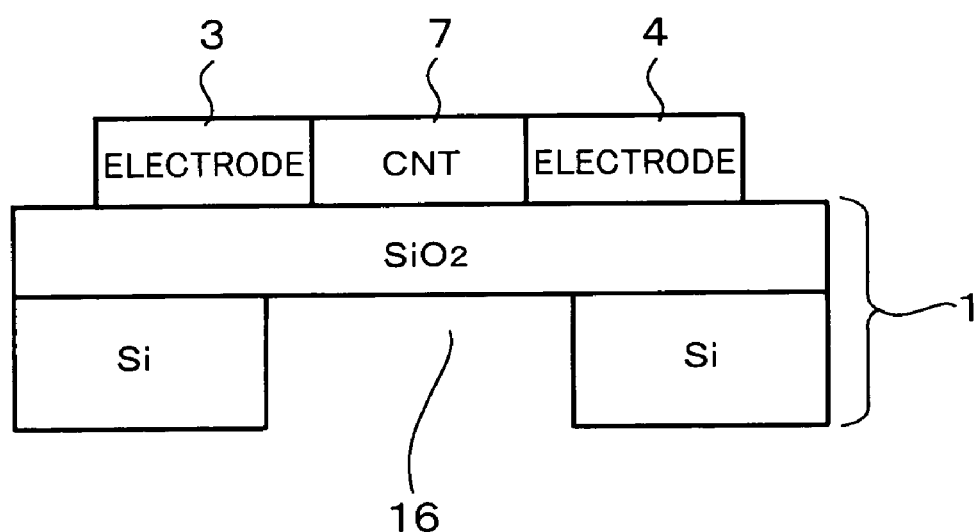
FIG. 19 is a schematic configuration view showing another structure of the sensor according to the present invention.

FIG. 19 is a schematic configuration view for explaining further another structure. In this structure, the substrate 1 itself is used as a channel (back channel), and the electrodes 3 and 4 are provided on the substrate 1 so as to put the CNTs 7 therebetween. A recess portion 16 serving as a channel is formed in the back surface of the substrate 1. When the recess portion 16 is wet with a liquid containing a to-be-detected substance, the to-be-detected substance can be detected by the back surface of the substrate 1.

Figure 20:
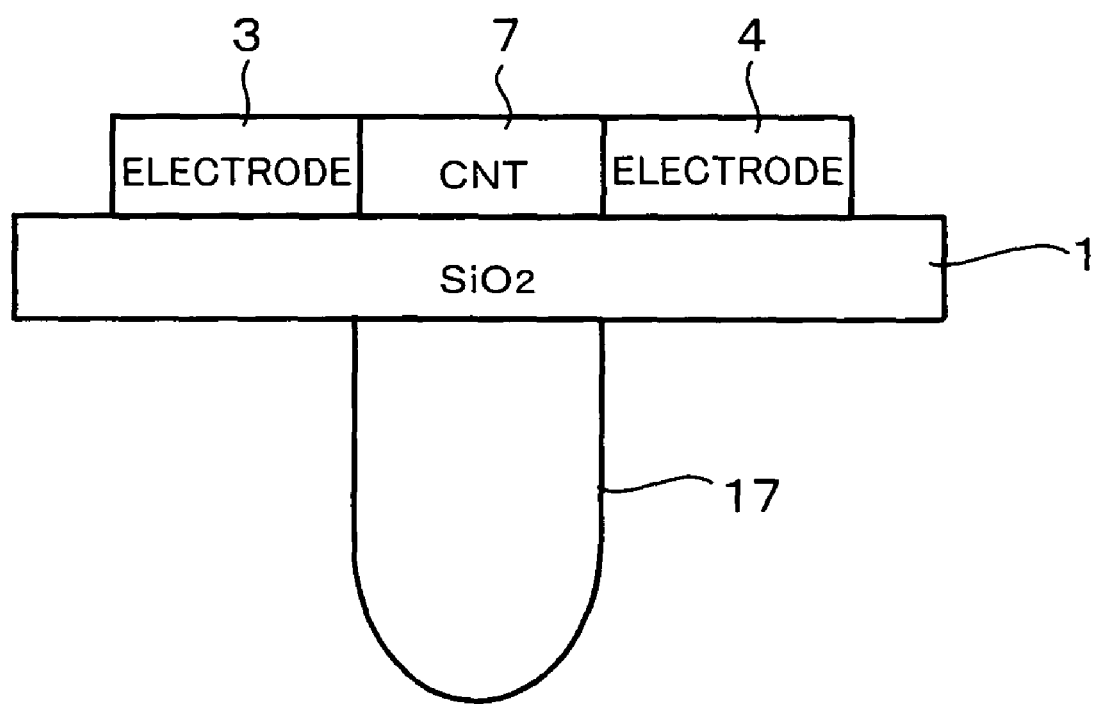
FIG. 20 is a schematic configuration view showing further another structure of the sensor according to the present invention.

FIG. 20 is a schematic configuration view for explaining further another structure. Also in this structure, the substrate 1 itself is used as a channel (back channel), and a probe 17 made of CNTs or the like is provided in the channel of the substrate 1. This integrated combination of the back channel and the probe 17 can be, for example, used as a probe of a scanning probe microscope or the like.

Figure 21:
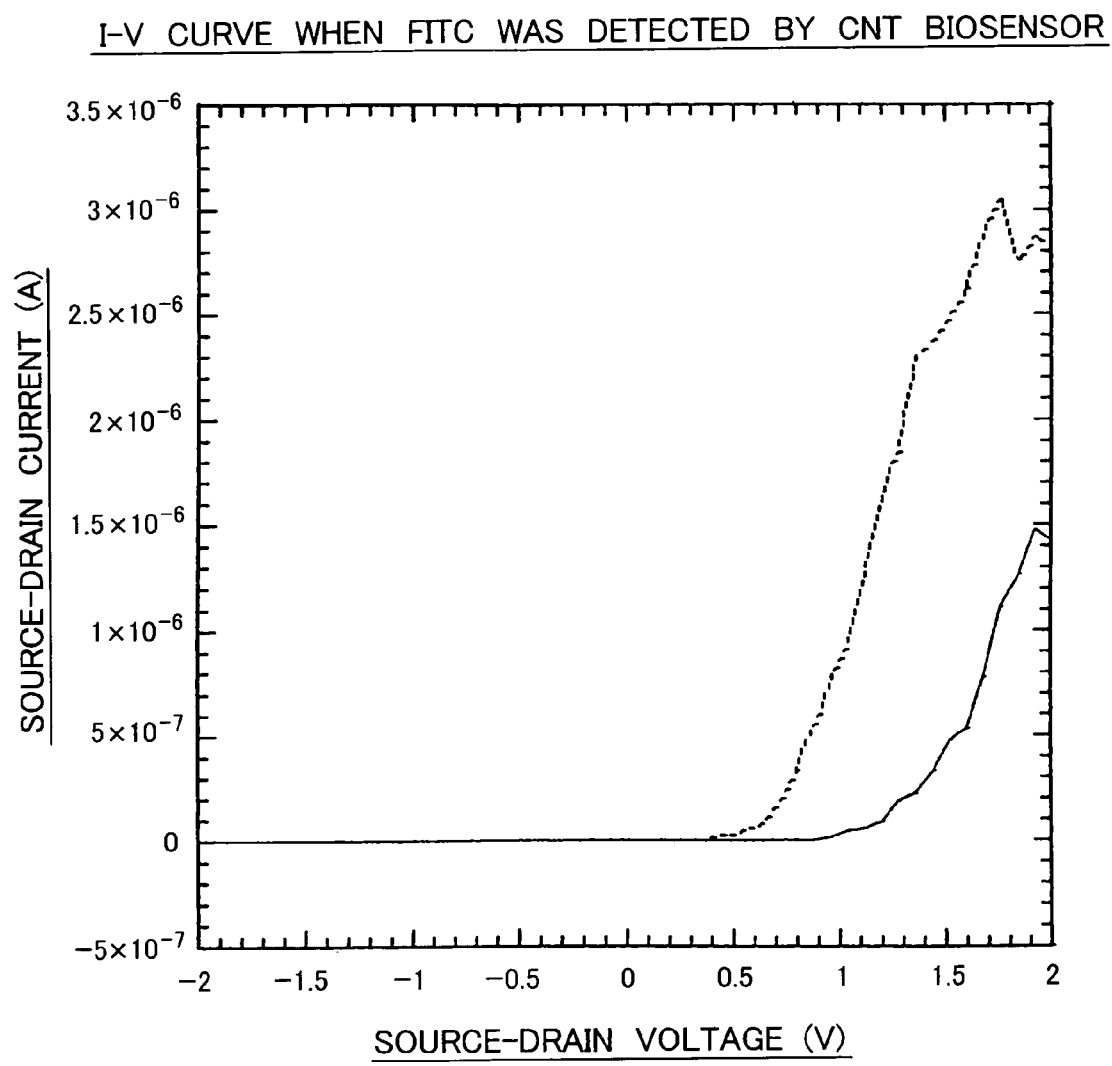
FIG. 21 is an I-V characteristic curve graph when FITC was detected by the sensor according to the present invention.

Next, description will be made on specific examples of the present invention. As a pilot study, a solution containing a fluorescent molecule FITC was dropped onto an SiO2 film back gate electrode, and a change in current characteristic was measured. FIG. 21 shows the I-V characteristic when the gate voltage was set at −20 V and the concentration of the fluorescent molecule FITC was set at 0.64 nM. In FIG. 21, the abscissa designates a value (A) of a current flowing between the source electrode and the drain electrode, and the ordinate designates a value of a voltage (V) between the source electrode and the drain electrode. In FIG. 21, the broken line designates the I-V characteristic curve before the fluorescent molecule FITC was attached, and the solid line designates the I-V characteristic curve after the fluorescent molecule FITC was attached. As is apparent from FIG. 21, there is a large change between the I-V characteristics before and after the fluorescent molecule FITC was attached.

EXAMPLE 1

Figure 22:
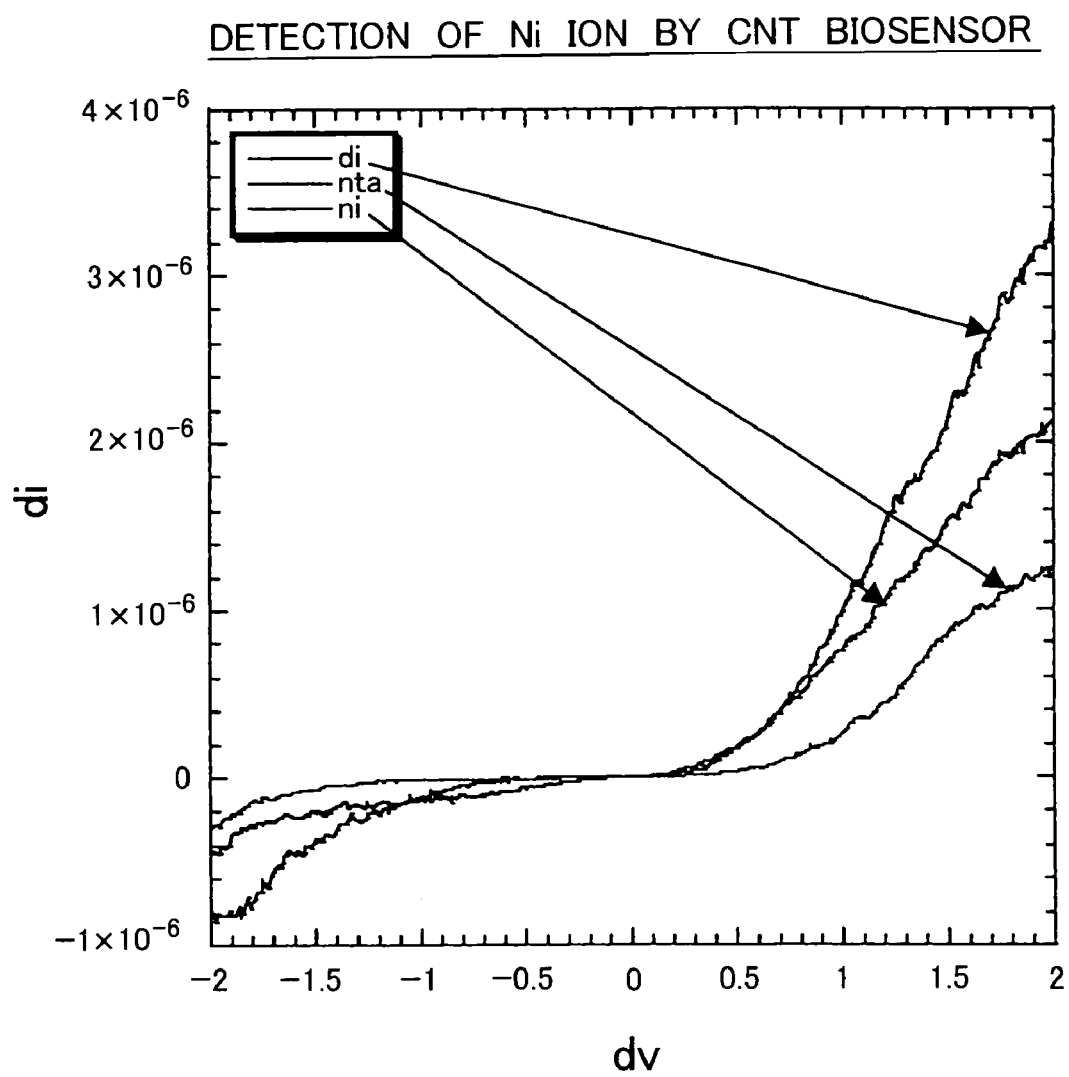
FIG. 22 is an I-V characteristic curve graph when an Ni ion was detected by the sensor according to the present invention.
Figure 23:
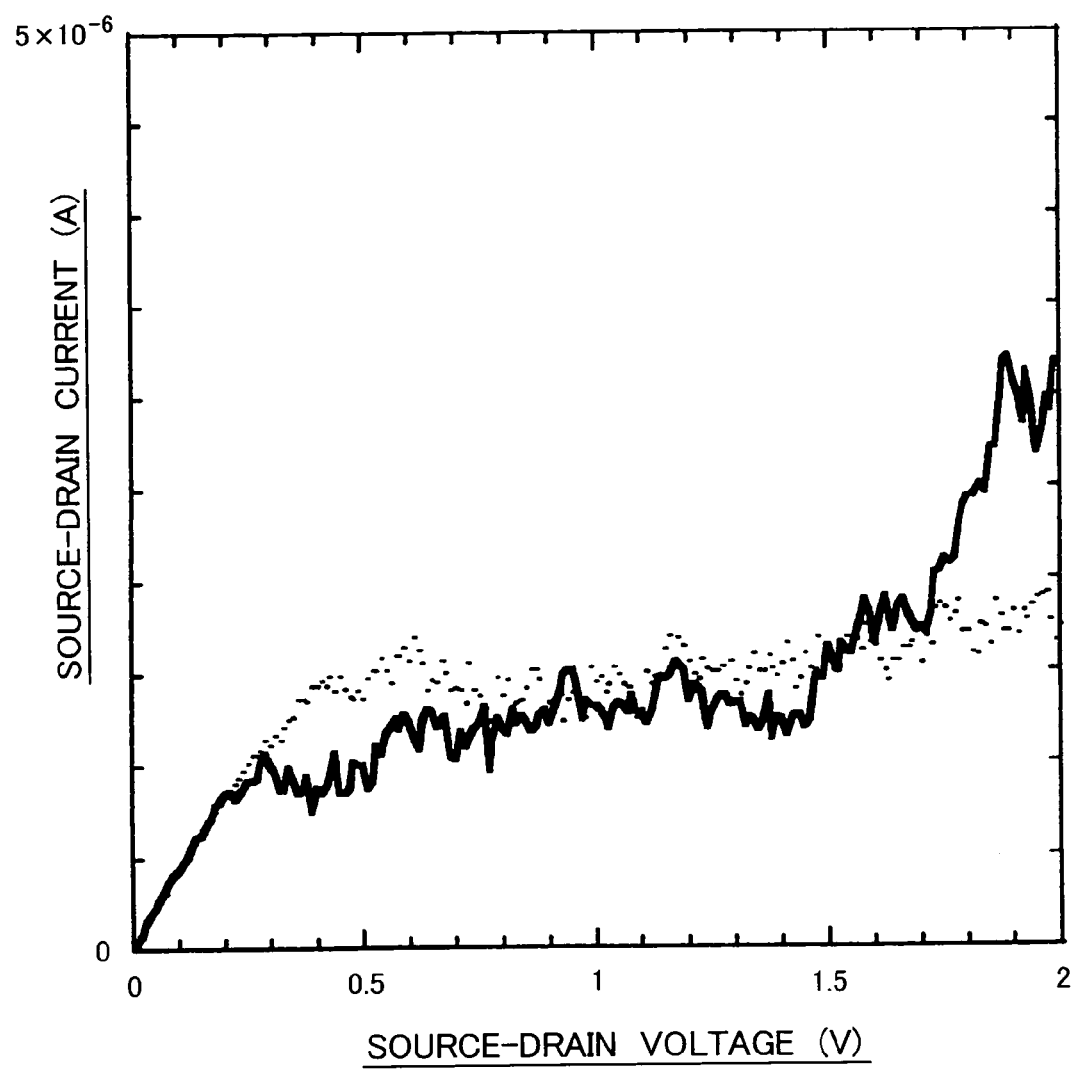
FIG. 23 is an I-V characteristic curve graph when hemagglutinin was detected by antigen-antibody reaction of the sensor according to the present invention.
Figure 24:
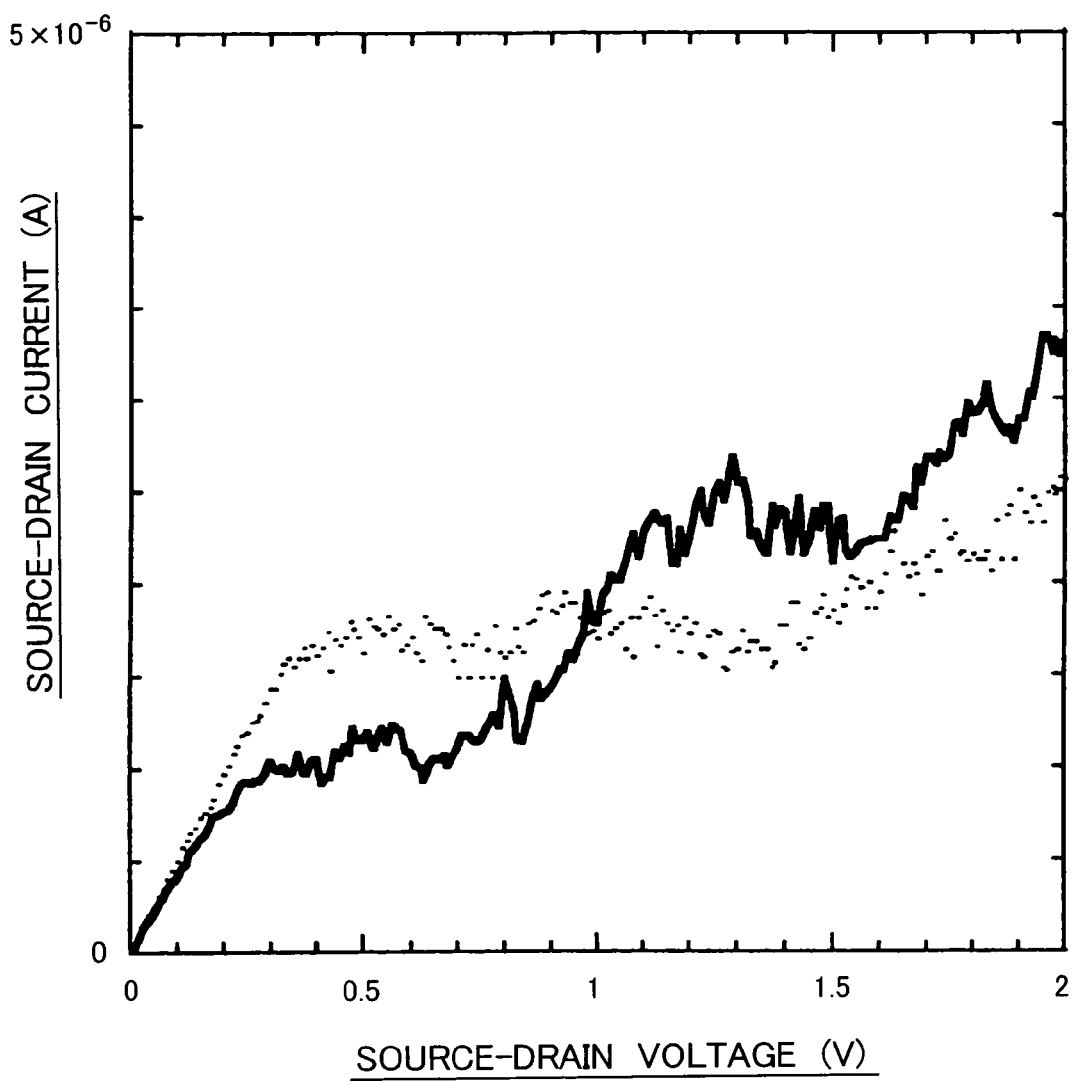
FIG. 24 is an I-V characteristic curve graph when hemagglutinin was detected by antigen-antibody reaction of the sensor according to the present invention.
Figure 25:
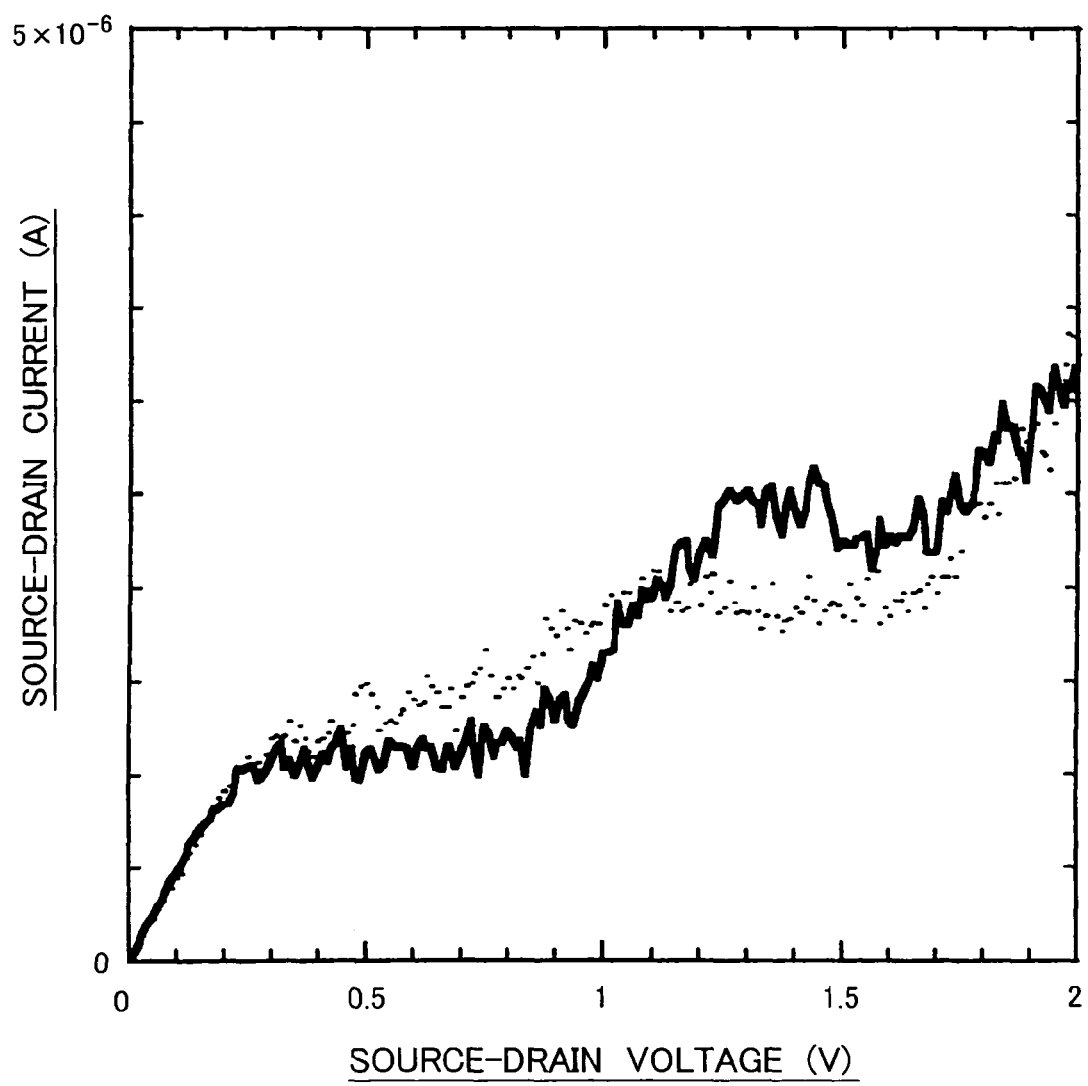
FIG. 25 is an I-V characteristic curve graph when hemagglutinin was detected by antigen-antibody reaction of the sensor according to the present invention.
Figure 26:
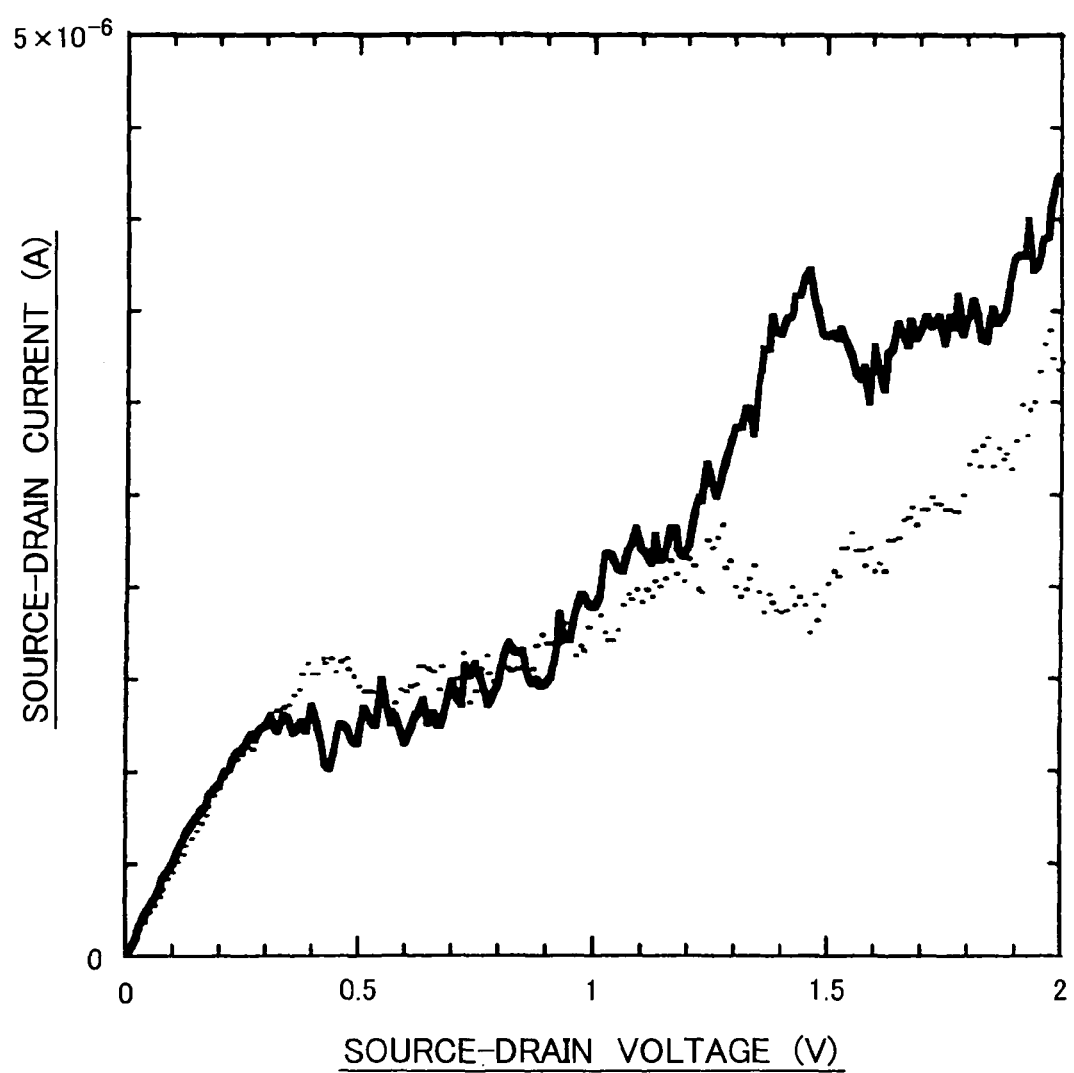
FIG. 26 is an I-V characteristic curve graph when hemagglutinin was detected by antigen-antibody reaction of the sensor according to the present invention.
Figure 27:
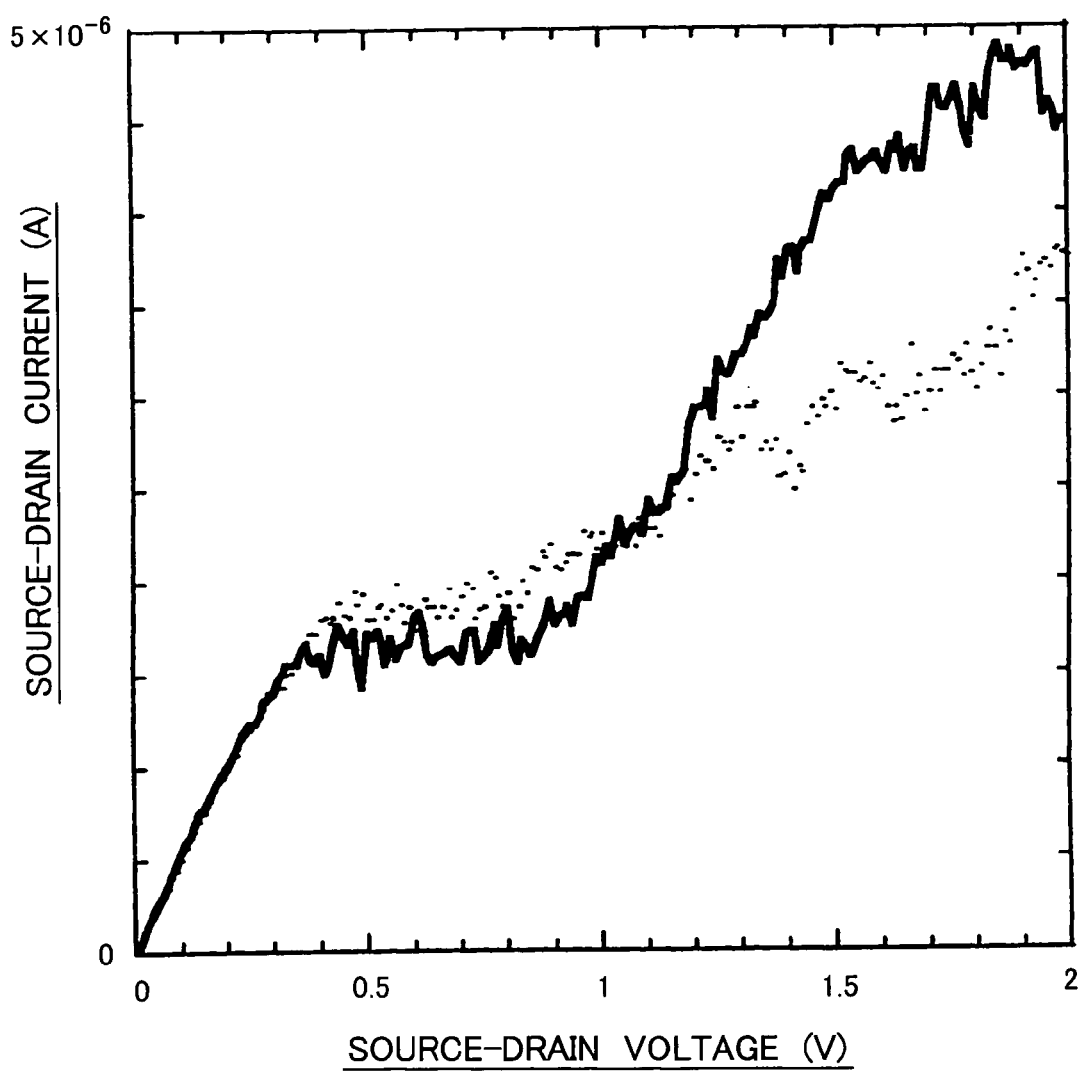
FIG. 27 is an I-V characteristic curve graph when hemagglutinin was detected by antigen-antibody reaction of the sensor according to the present invention.
Figure 28:
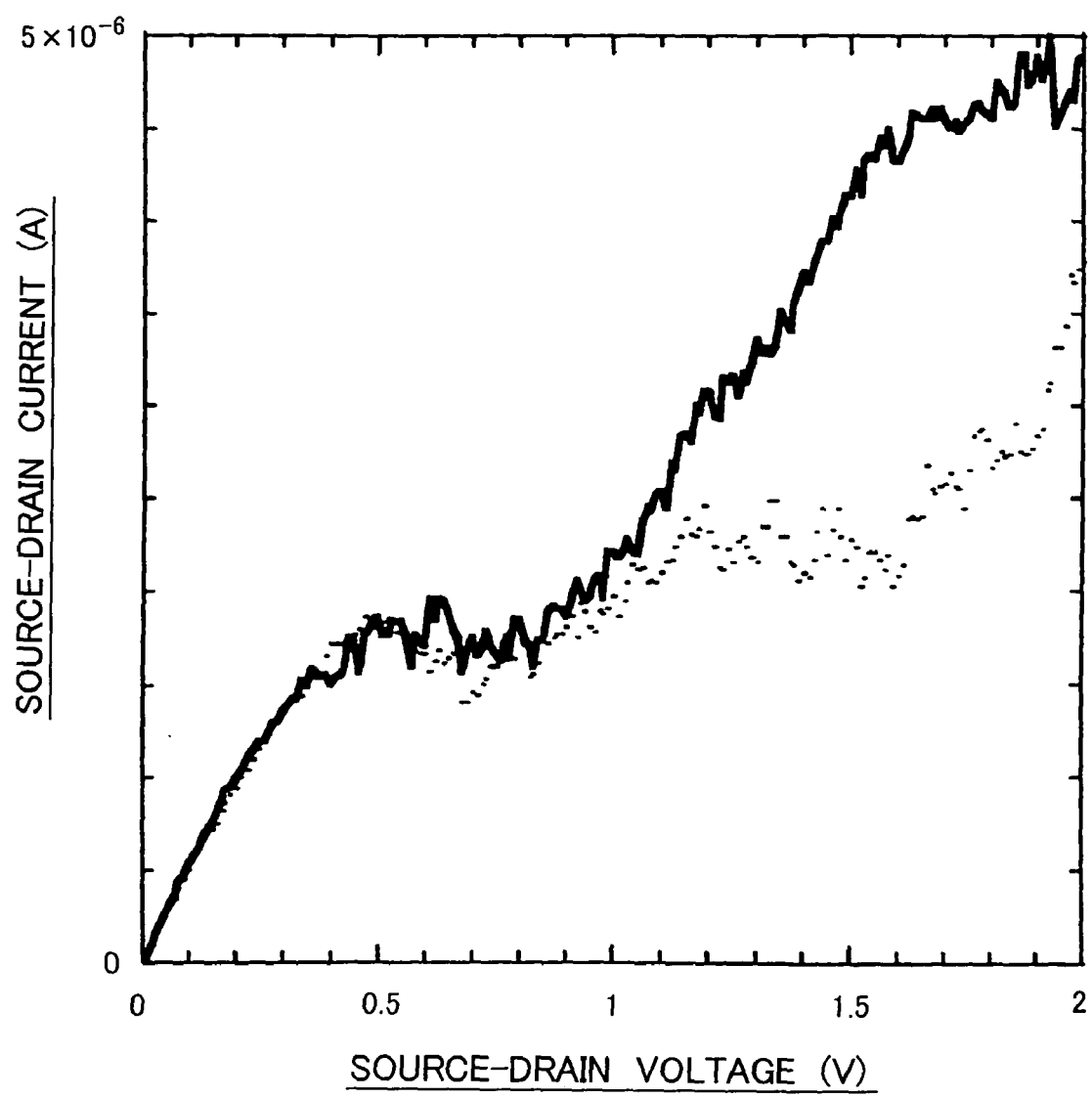
FIG. 28 is an I-V characteristic curve graph when hemagglutinin was detected by antigen-antibody reaction of the sensor according to the present invention.

Next, description will be made on detection of a divalent ion using ionic reaction. CNTs of a CNT biosensor was modified directly by pyrene, and {N-[5-(3'-Maleimidopropylamino)-1-carboxypentyl]iminodiacetic acid: hereinafter abbreviated to NTA} was bonded with a back gate electrode. After that, a solution containing Ni ions was dropped, and the conduction characteristic was examined based on the I-V characteristic in each case. FIG. 22 shows the I-V characteristics when no electric field was applied to the gate electrode. The abscissa designates a value (A) of a current flowing between the source electrode and the drain electrode, and the ordinate designates a value (V) of a voltage between the source electrode and the drain electrode. In FIG. 22, di designates the I-V characteristic curve after the back gate electrode was cleaned, nta designates the I-V characteristic curve after NTA was bonded, and ni designates the I-V characteristic curve after the solution containing Ni ions was dropped.

As is apparent from FIG. 22, when the voltage between the source electrode and the drain electrode was increased, the current increased, but the current rarely increased near dv=0 V in all the systems (systems of di, nta and ni). That is, semiconductor-like properties were observed.

The I-V characteristic curve after NTA was bonded with the back gate electrode showed remarkable reduction in current as compared with the I-V characteristic curve after the back gate electrode was cleaned. In contrast, when Ni ions were added to the system, the current increased. NTA reacts with not only Ni ions but also divalent plus ions. Accordingly, other divalent plus ions can be detected likewise.

EXAMPLE 2

Next, description will be made on detection of H9 hemagglutinin (HA) using antigen-antibody reaction. C-terminus of HA was cut in various levels (220, 250, 290 and 320), and expression was attempted. Genes were introduced into a 293T cell, and expression of HA protein in the cell was confirmed using a monoclonal antibody E2/3 and a polyclonal antibody. Secretion of the HA protein in supernatant was confirmed by a western blotting method. Plenty of HA1-290 was expressed and refined from the supernatant by Ni2 and a column. A fraction including the intended HA protein was confirmed by ELISA and SDS-PAGE, and this fraction was fractionated and dialyzed by PBS so as to obtain the HA. Expression could be observed as to shorter HA1-220. However, the HA creased from reaction with the monoclonal antibody. Therefore, the HA was not used.

NTA was bonded with the SiO2 film back gate electrode of the CNT biosensor. After that, Ni ions were added to the system, and HA antibodies having concentrations ranged from 10-10 to 10-5 in dilution ratio with respect to a stock solution were applied. Thus, I-V characteristic curves were obtained. In this event, HA was absent from the back gate electrode. Therefore, the HA antibodies were not bonded to have orientation on the back gate electrode.

Next, the HA was fixed to NTA on the SiO2 film back gate electrode by His tag attached in advance. HA antibodies were applied likewise, and I-V characteristic curves were obtained. These I-V characteristic curve graphs are shown in FIGS. 23-28. Incidentally, the gate voltage was set to be −20 V.

FIG. 23 is an I-V characteristic curve graph when the solution containing Ni ions was applied after NTA was bonded. FIG. 24 is an I-V characteristic curve graph when the HA antibody having a dilution ratio of 10-10 with respect to a stock solution was applied. FIG. 25 is an I-V characteristic curve graph when the HA antibody having a dilution ratio of 10-8 with respect to a stock solution was applied. FIG. 26 is an I-V characteristic curve graph when the HA antibody having a dilution ratio of 10-7 with respect to a stock solution was applied. FIG. 27 is an I-V characteristic curve graph when the HA antibody having a dilution ratio of 10-6 with respect to a stock solution was applied. FIG. 28 is an I-V characteristic curve graph when the HA antibody having a dilution ratio of 10-5 with respect to a stock solution was applied.

In each of these graphs, the broken line designates the aforementioned former in which the HA was absent from the SiO2 film back gate electrode, and the solid line designates the aforementioned latter in which the HA was fixed to NTA on the SiO2 film back gate electrode by His tag attached in advance.

As is apparent from these graphs, little difference in current value between the source electrode and the drain electrode was observed between the both (solid line and broken line) when the voltage between the source electrode and the drain electrode was varied from 0 V to 1 V. However, when the voltage was increased to 1 V or higher, the characteristic in which the current value increased suddenly was shown in the system (solid line) where the HA was regarded as fixed.

From this fact, it is understood that the HA antibody can be detected even in an area of high dilution ratio as compared with the background-art method such as ELISA (Enzyme-Linked ImmunoSorbent Assay).

EXAMPLE 3

As for such detection of H9 hemagglutinin (HA) using antigen-antibody reaction, similar results could be obtained by use of a sol-gel method. I-V characteristics obtained thus are shown in FIGS. 29-34. Incidentally, in all the systems before testing of antigen-antibody reaction, a solution containing Ni ions was applied after NTA was bonded. The gate voltage was set to be −20 V.

Figure 29:
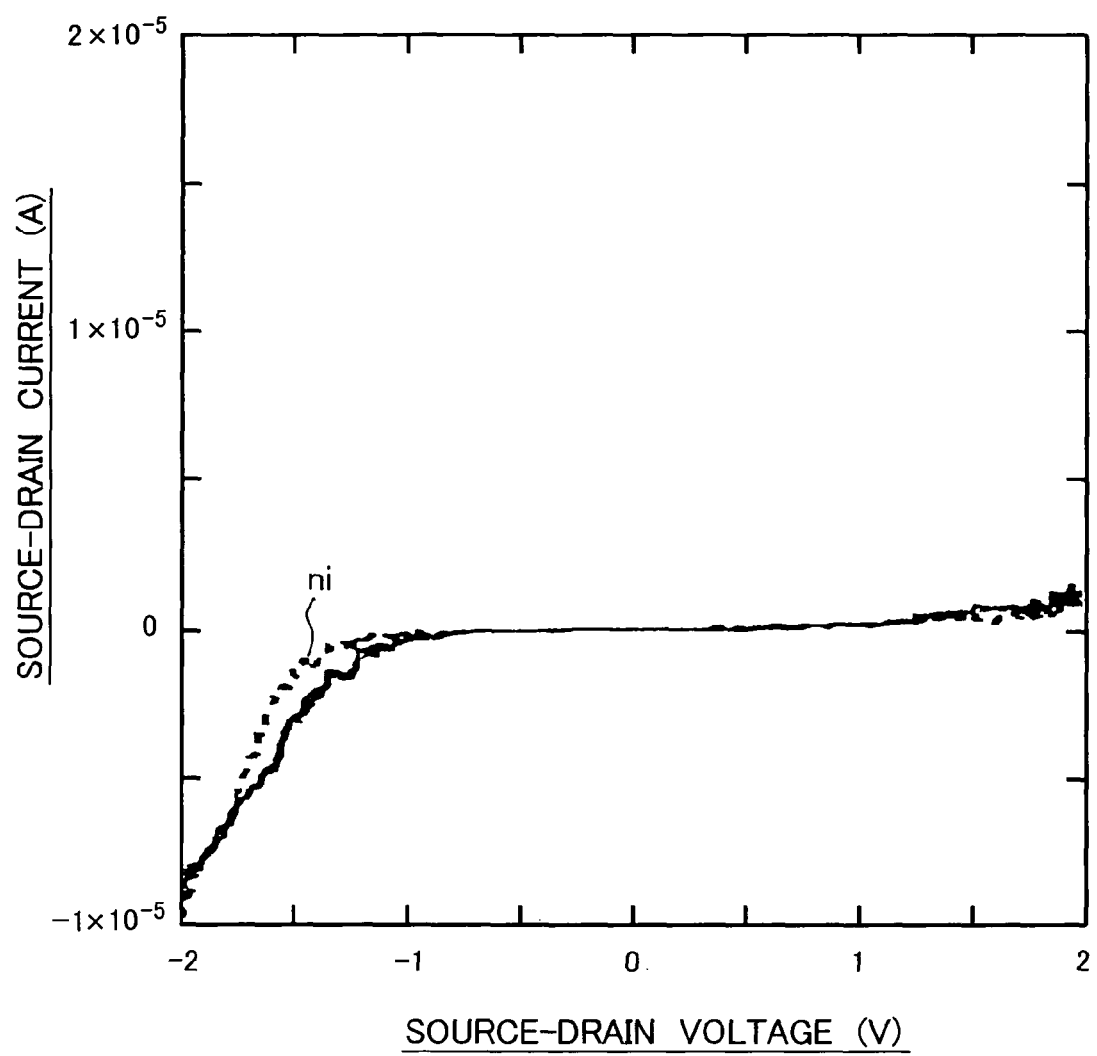
FIG. 29 is an I-V characteristic curve graph when hemagglutinin was detected by antigen-antibody reaction in a sol-gel method of the sensor according to the present invention.
Figure 30:
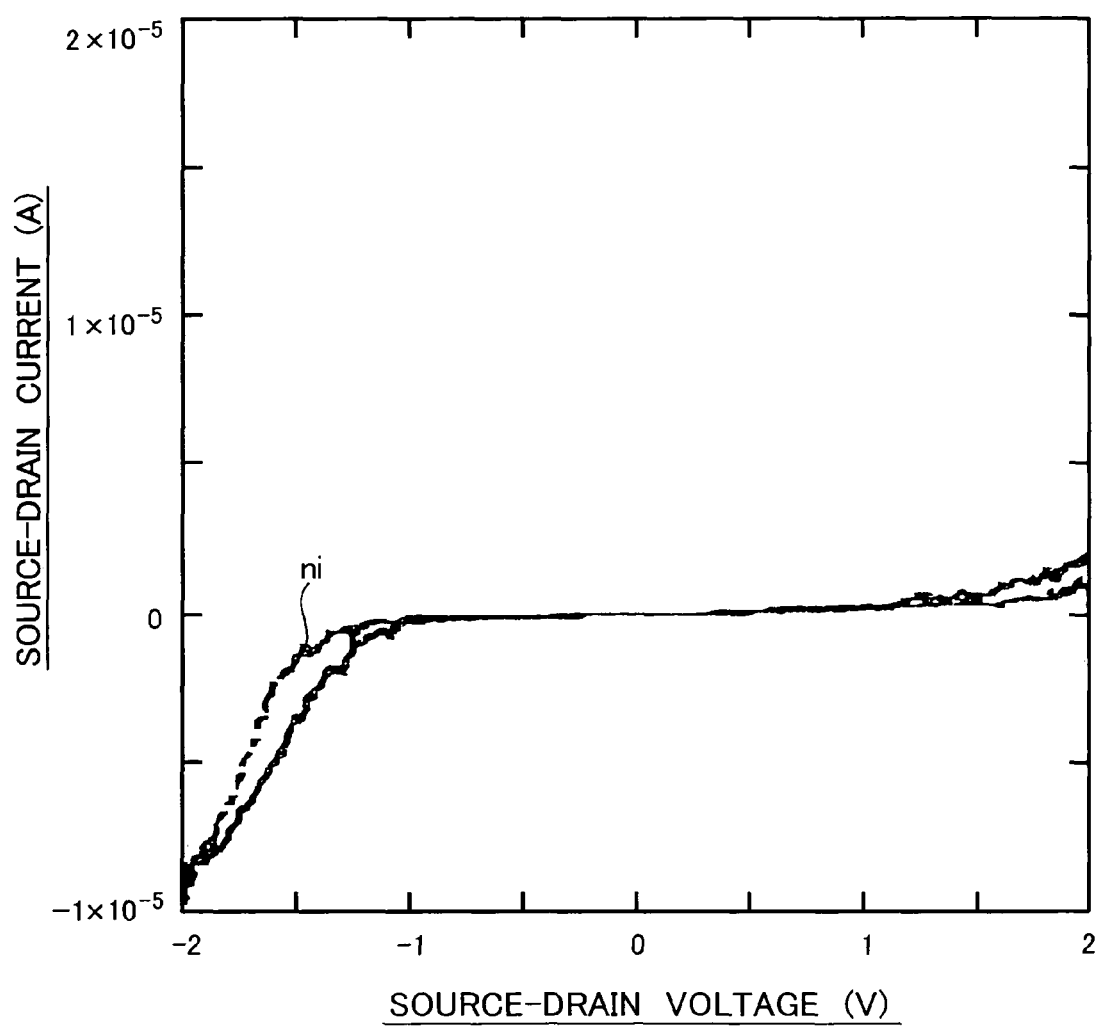
FIG. 30 is an I-V characteristic curve graph when hemagglutinin was detected by antigen-antibody reaction in a sol-gel method of the sensor according to the present invention.
Figure 31:
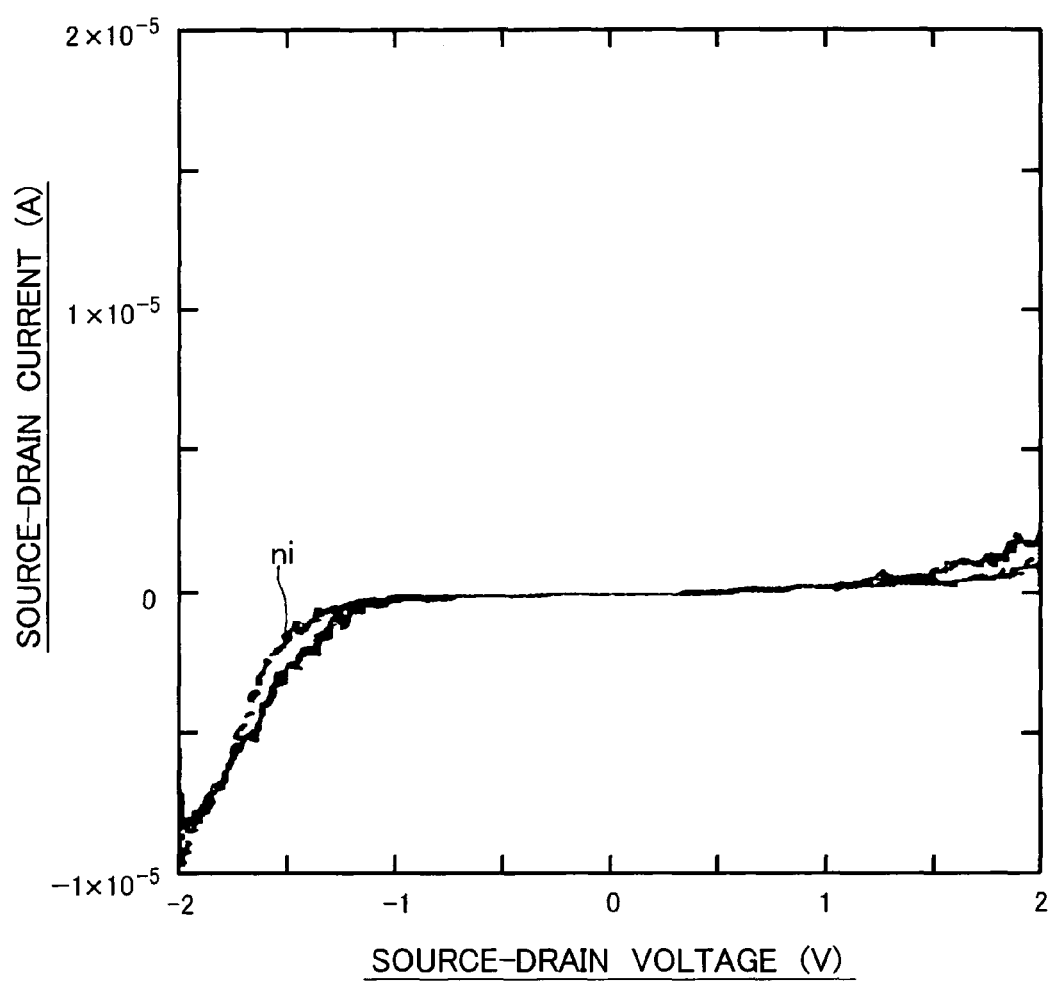
FIG. 31 is an I-V characteristic curve graph when hemagglutinin was detected by antigen-antibody reaction in a sol-gel method of the sensor according to the present invention.
Figure 32:
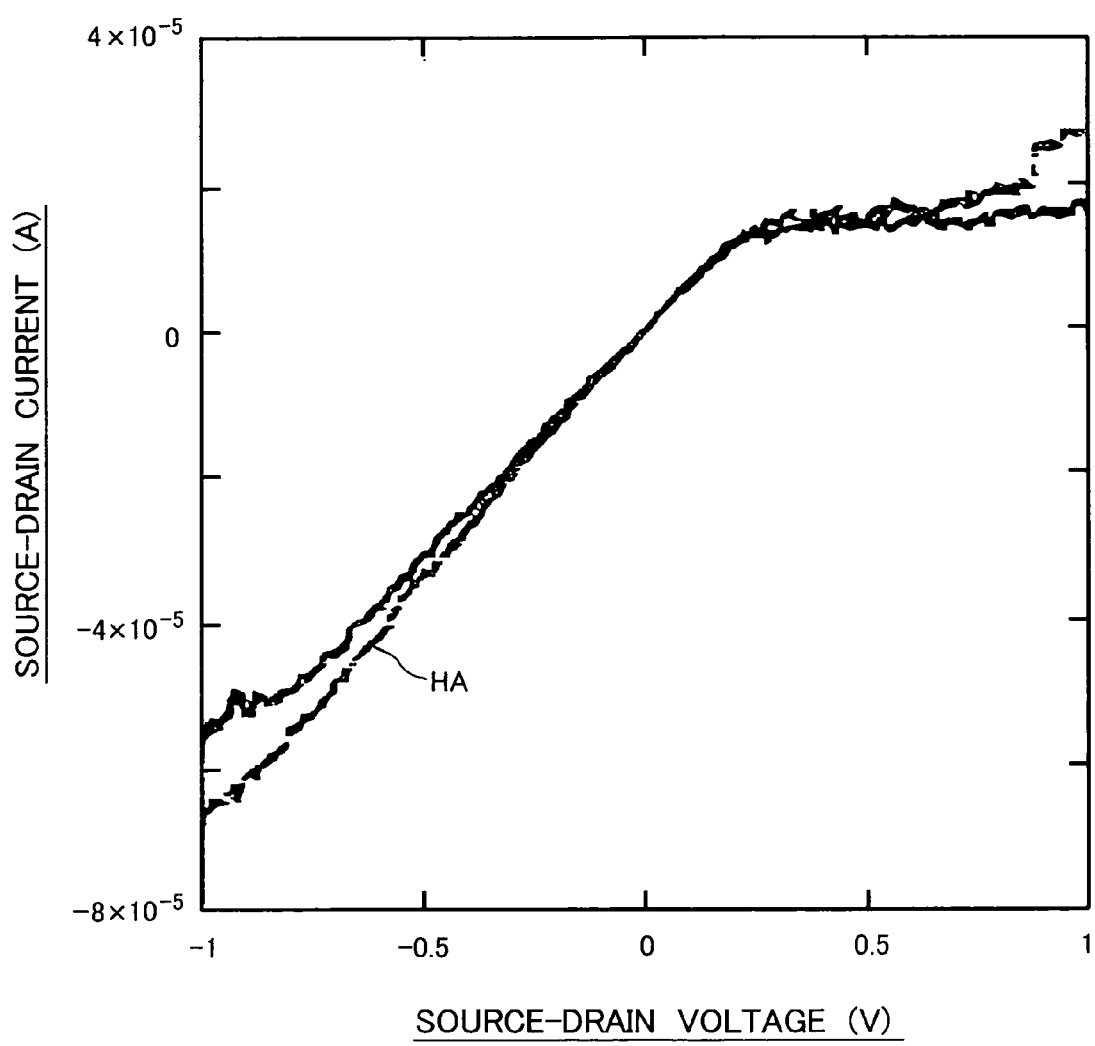
FIG. 32 is an I-V characteristic curve graph when hemagglutinin was detected by antigen-antibody reaction in a sol-gel method of the sensor according to the present invention.
Figure 33:
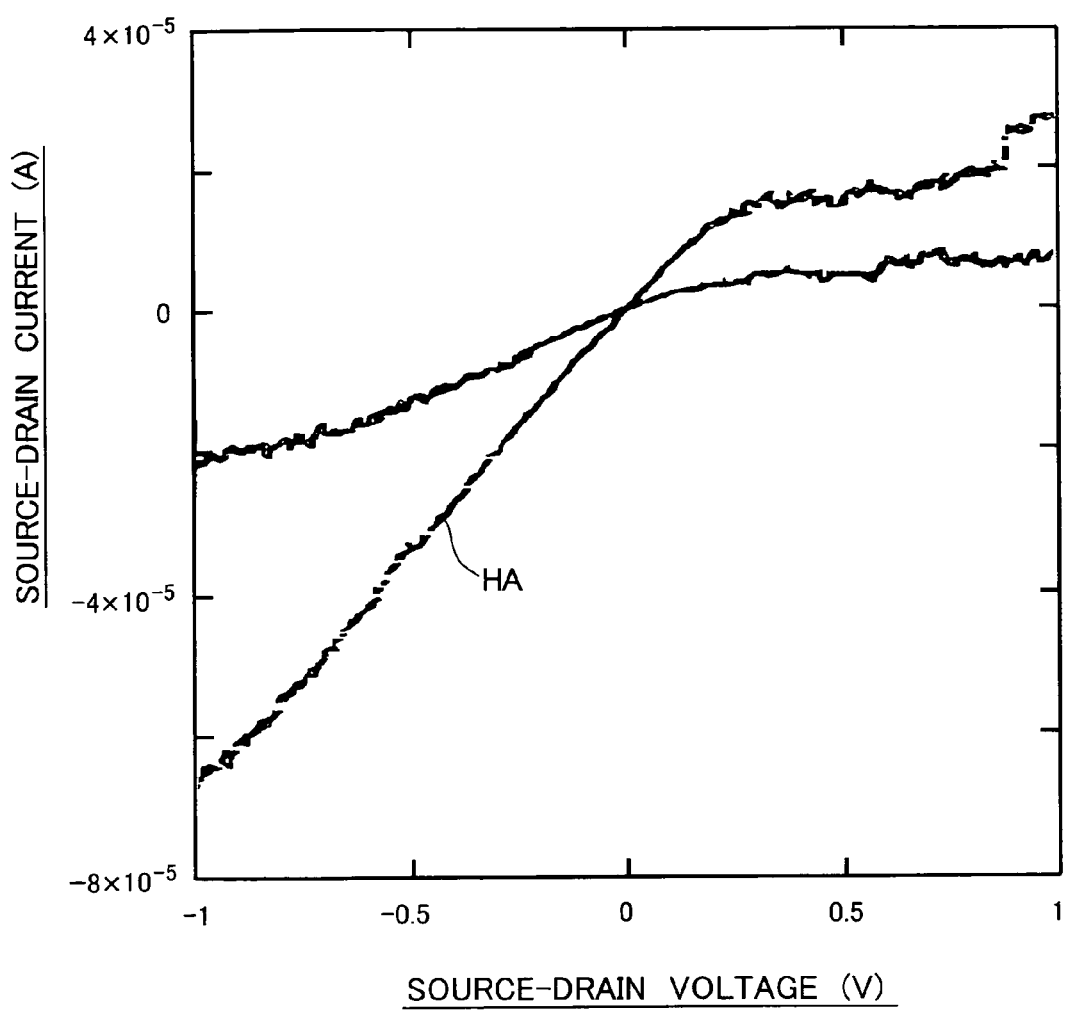
FIG. 33 is an I-V characteristic curve graph when hemagglutinin was detected by antigen-antibody reaction in a sol-gel method of the sensor according to the present invention.
Figure 34:
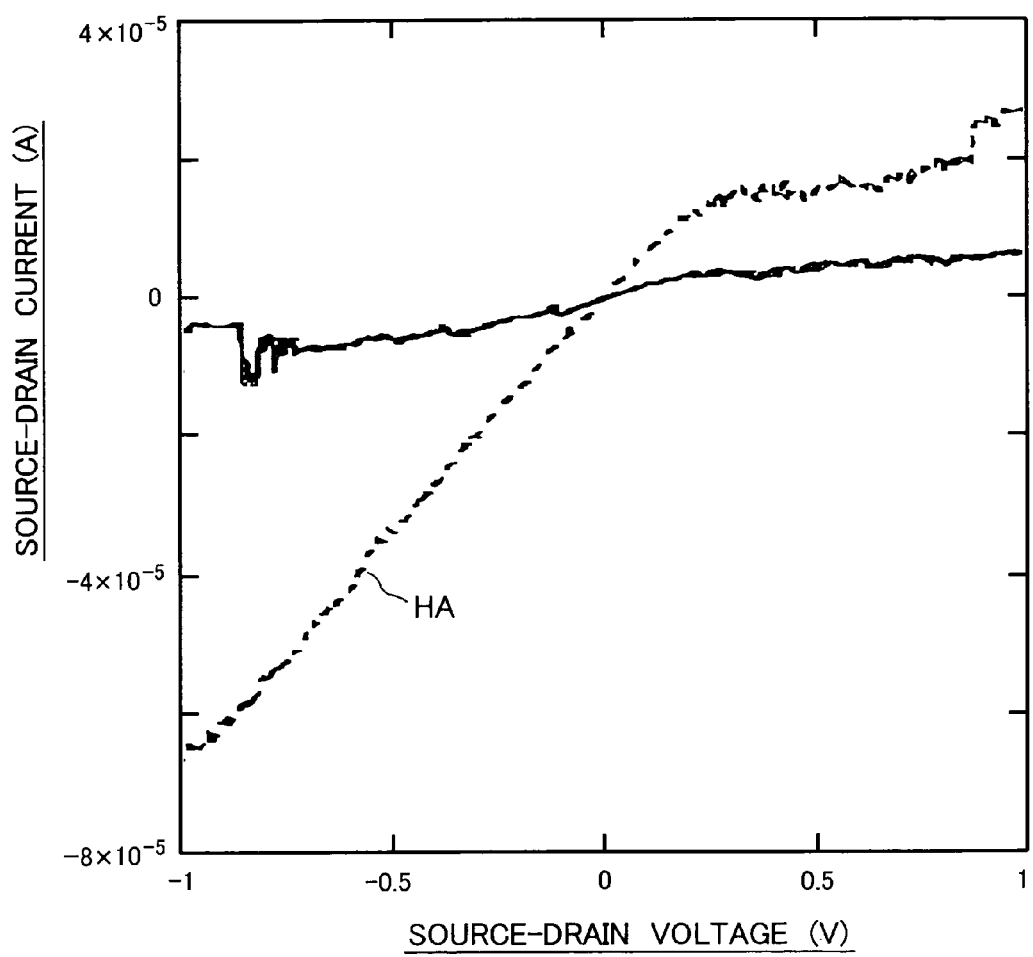
FIG. 34 is an I-V characteristic curve graph when hemagglutinin was detected by antigen-antibody reaction in a sol-gel method of the sensor according to the present invention.

FIG. 29 is an I-V characteristic curve graph when the HA antibody having a dilution ratio of $10^{-7}$ was applied without attaching the HA antigen. FIG. 30 is an I-V characteristic curve graph when the HA antibody having a dilution ratio of $10^{-6}$ was applied without attaching the HA antigen. FIG. 31 is an I-V characteristic curve graph when the HA antibody having a dilution ratio of $10^{-5}$ was applied without attaching the HA antigen. FIG. 32 is an I-V characteristic curve graph when the HA antibody having a dilution ratio of $10^{-6}$ was applied after attaching the Ha antigen. FIG. 33 is an I-V characteristic curve graph when the HA antibody having a dilution ratio of $10^{-5}$ was applied after attaching the HA antigen. FIG. 34 is an I-V characteristic curve graph when the HA antibody having a dilution ratio of $10^{-4}$ was applied after attaching the HA antigen.

In each of these graphs, ni designates an I-V characteristic curve when the solution containing Ni ions was applied after NTA was bonded, and HA designates an I-V characteristic curve in which the HA was fixed to NTA on the $SiO_2$ film back gate electrode by His tag attached in advance.

As is apparent from these graphs, there appeared a great change in current value between the source electrode and the drain electrode particularly when the dilute ratio with respect to the stock solution was $10^{-5}$ and $10^{-4}$. The detection sensitivity was almost as high as that in ELISA.

EXAMPLE 4

Next, description will be made on detection of calmodulin (CaM) using antigen-antibody reaction. A DNA fragment containing rat calmodulin gene cDNA was inserted into a SacI-XbaI site of an expression vector pBAD/gIII (made by Invitrogen Corporation) so as to assemble a calmodulin expression vector (pBAD/gIII/calmodulin). The vector was introduced into a *Escherichia coli* LMG194. Thus, a calmodulin expression clone was obtained. This clone was planted in an LB/Ampicilin medium of 2 ml, and cultured for one night.

5 ml of this culture solution was inoculated into an LB/Ampicilin medium, and subjected to shaking culture at 37° C. till OD600 reached 0.5. After that, L-arabinose was added so that the final concentration was 0.02%. Shaking culture was further performed at 37° C. for 4 hours. The cultured cells were collected by centrifugal collection, suspended by Native Binding Buffer (made by Invitrogen Corporation), crushed ultrasonically, partially refined by use of Probond™ Purification System (made by Invitrogen Corporation), and then refined uniformly like SDS/polyacrylamide electrophoresis by use of Hi Load 26/60 Superdex 75 pg (made by Amersham Bioscience Corp.). Thus, calmodulin was obtained.

Figure 35:
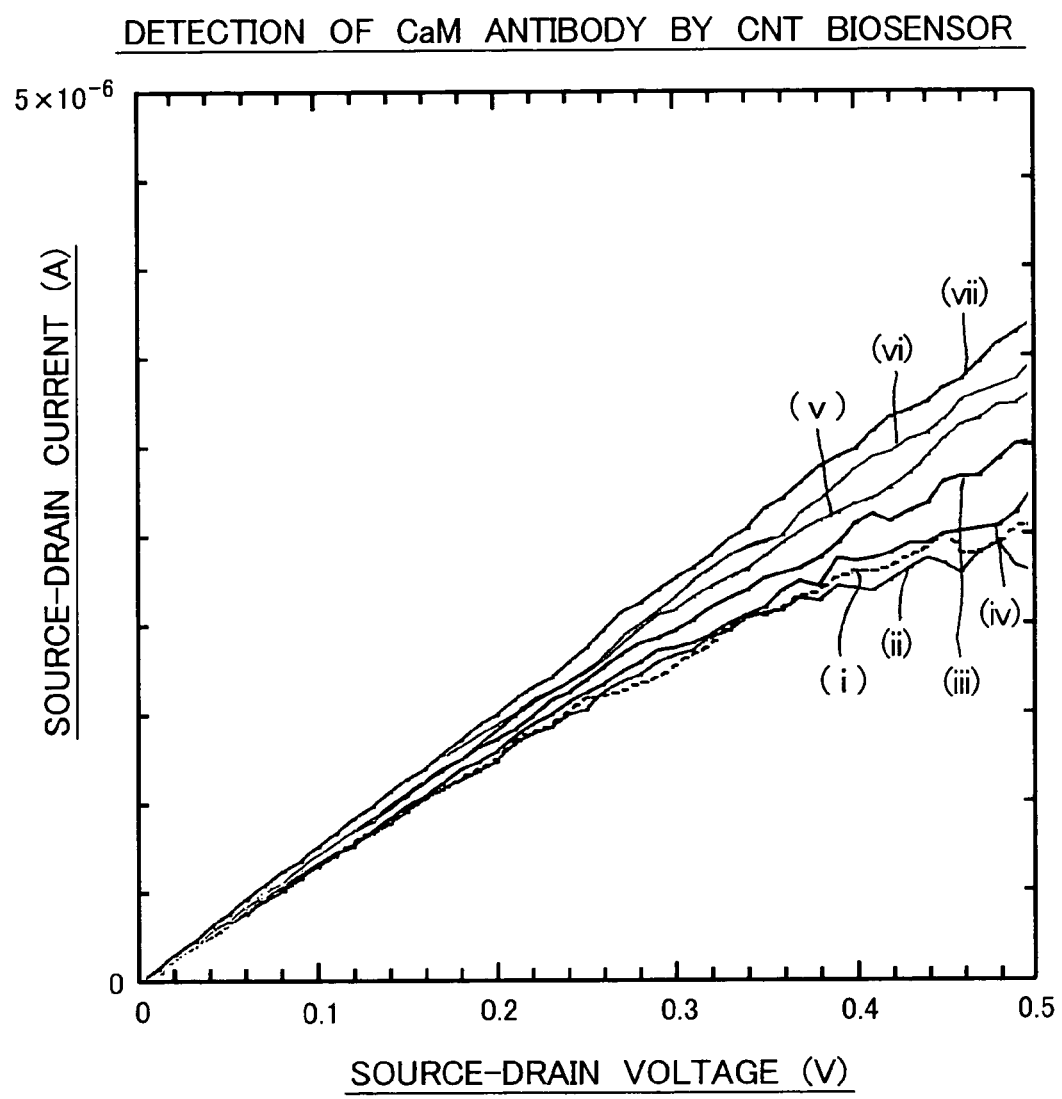
FIG. 35 is an I-V characteristic curve graph when calmodulin was detected by antigen-antibody reaction of the sensor according to the present invention.

NTA was bonded to the $SiO_2$ film back gate electrode of the CNT biosensor. After that, the HA was fixed to NTA on the $SiO_2$ film back gate electrode by His tag attached in advance. HA antibodies having dilution ratios ranging from $10^{-8}$ to $10^{-2}$ with respect to a stock solution were applied, and I-V characteristic curves were obtained. The results are shown in FIG. 35. Incidentally, the gate voltage was set to be −20 V.

In FIG. 35, a curve (i) designates an I-V characteristic curve when cleaning was performed after NTA was bonded, a curve (ii) designates an I-V characteristic curve when CaM was bonded to NTA by His tag attached in advance, a curve (iii) designates an I-V characteristic curve when the CaM antibody having a dilution ratio of $10^{-8}$ with respect to a stock solution was applied, a curve (iv) designates an I-V characteristic curve when the CaM antibody having a dilution ratio of $10^{-7}$ with respect to a stock solution was applied, a curve (v) designates an I-V characteristic curve when the CaM antibody having a dilution ratio of $10^{-6}$ with respect to a stock solution was applied, a curve (vi) designates an I-V characteristic curve when the CaM antibody having a dilution ratio of $10^{-4}$ with respect to a stock solution was applied, and a curve (vii) designates an I-V characteristic curve when the CaM antibody having a dilution ratio of $10^{-2}$ with respect to a stock solution was applied.

As is apparent from FIG. 35, the current value changed in accordance with each concentration when the voltage between the source electrode and the drain electrode was varied from 0 V to 0.5 V. From this fact, it is understood that the CMA antibody can be detected even in an area of very high dilution ratio with respect to the stock solution in the same manner as the HA antibody.

The results of detection of CaM antibodies and HA antibodies using ELISA are shown in the following table. Incidentally, in this measuring procedure, a primary antibody was diluted at the following dilution ratio and made to stand still for one hour. A secondary antibody (antimouse HRPO standard antibody) was diluted 5,000 times and made to stand still for one hour again. A substrate having an absorption wavelength of 450 nm was produced by a TMB color former, and the absorbance was measured.

TABLE

|  |  | (CaM antibody) | (HA antibody) |
|---|---|---|---|
| PBS | Neg. Con | 0.034 | 0.030 |
|  | $2.5 \times 10^{-2}$ | 2.000 | 1.722 |
|  | $6.3 \times 10^{-3}$ | 2.439 | 2.725 |
|  | $1.6 \times 10^{-3}$ | 2.899 | 3.378 |
|  | $3.9 \times 10^{-4}$ | 2.300 | 3.132 |
|  | $0.98 \times 10^{-4}$ | 0.650 | 2.839 |
|  | $2.4 \times 10^{-5}$ | 0.177 | 1.413 |
|  | $6.1 \times 10^{-6}$ | 0.051 | 0.290 |

It is proved that detection becomes difficult in the dilution ratio of $6.1 \times 10^{-6}$ by ELISA. On the other hand, in the aforementioned Examples 3 and 4, the sol-gel method shows the sensitivity as high as ELISA, while detection is successful in the dilution ratio of about $10^{-8}$ in the other methods.

CNTs were grown on an Si substrate, and electrodes were formed on the opposite end portions thereof. The back surface of the aforementioned Si substrate on the opposite side to the surface where the CNTs were grown was activated by acid (sulfuric acid). After that, NTA was fixed by reaction with a silanizing reagent (3-mercaptopropyltrimethoxysilane) at 180° C. Next, Ni ions were added to fix an antigen (CaM, HA) histidine was introduced into. The fixed antigen was made to react with a diluted antibody. After that, the substrate was cleaned, and negative bias was applied to the back surface of the substrate. Thus, an I-V characteristic was measured.

Figure 36:
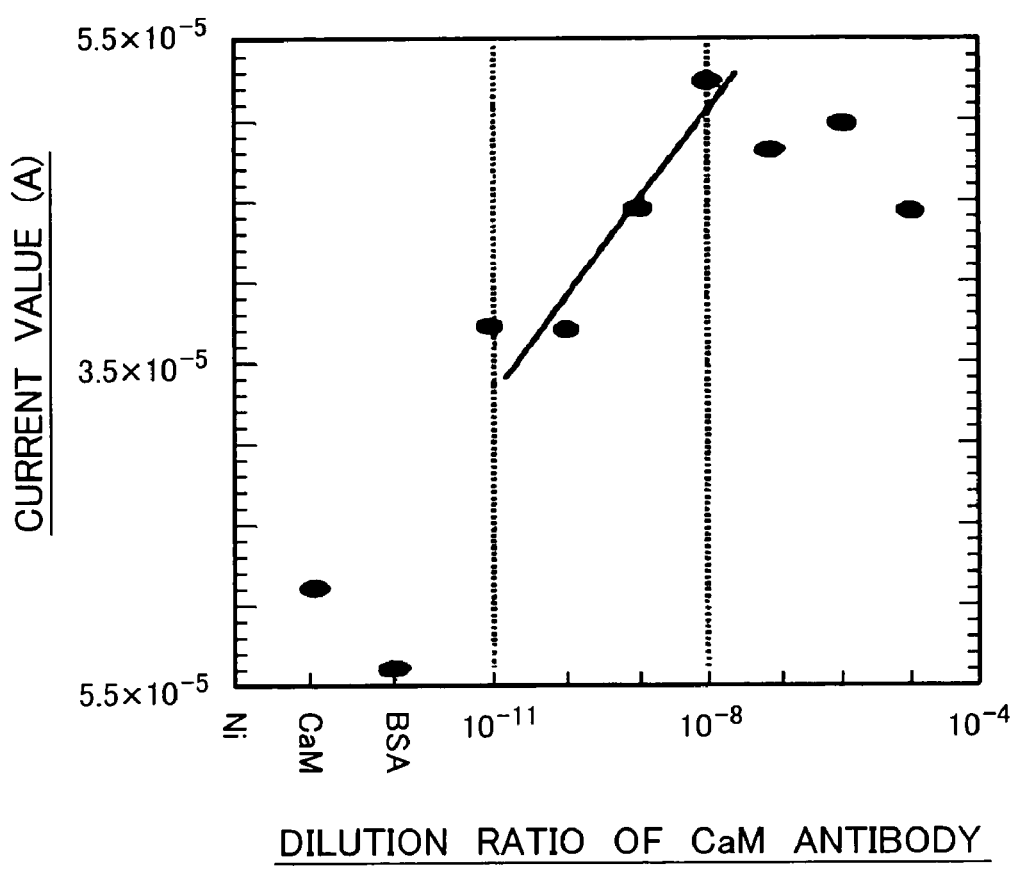
FIG. 36 is an I-V characteristic curve graph when calmodulin was detected by antigen-antibody reaction of the sensor according to the present invention.

FIG. 36 is a characteristic graph showing a change in current value when the CaM fixed as described above was made to react with the diluted CaM antibody and a voltage of 1.5 V was then applied between the CNT electrodes. As is apparent from FIG. 36, little change in current value was observed when the antigen was not fixed. However, the current value increased with the increase of the antibody concentration when the antigen was fixed. In addition, it was proved that the antibody could be detected in a range of dilution from about 10-10 to 10-8 with respect to the antibody stock solution.

When a detection limit of the same antibody by use of ELISA was examined, it was proved that there was a detection limit in the dilution of about 10-6 with respect to the antibody stock solution. It was also proved that there was a difference in detection limit between CaM and HA, and the detection limit depended on the antigen and the antibody.

Although the aforementioned Examples were described in the case where the gate voltage was −20 V, it has been proved that detection is successful in spite of a small change in current value even when the gate voltage is about 0 V or positive.

When the CNT biosensor is applied to a solution, there may occur a problem in reliability of data due to observation of noise. Therefore, after a sample solution (solution to be tested) is dropped onto the sensor, the solvent (moisture) may be evaporated by a blower, a heater, a thermoelectric conversion device (Peltier device), or the like. Thus, the noise can be reduced extremely. This countermeasure against the noise was applied to the aforementioned specific Examples to which a solution was applied. When the sample solution (solution to be tested) is cooled by a thermoelectric conversion device (Peltier device), liquid nitrogen or the like, the influence of the solvent such as water can be reduced. Particularly when water is frozen and insulated, the noise can be reduced on a large scale.

ELISA and Western blotting belong to the background-art methods. These methods have a limit of sensitivity in the dilution ratio of about 10-5 with respect to the stock solution. On the other hand, the sensitivity of the sensor according to the present invention is about 103 of that by ELISA as to detection of an HA antibody.

In addition, due to use of an electric signal, there are not many chemical reaction processes. Accordingly, the time required for detection is extremely short. According to examination of the current characteristic based on an I-V curve, the I-V curve can be acquired in several seconds by a parameter analyzer.

PCR or the like known in the background art is accompanied with a change in temperature. It is therefore necessary to control the temperature. However, the sensor according to the present invention can be used in an environment where the temperature is constant. Thus, temperature control is not required, but the configuration can be simplified and miniaturized. For example, an RT-PCR method, an ICAN method, a LAMP method, etc. can be used in an environment where the temperature is constant. However, any method has a problem that it takes long time for detection.

The sensor according to the present invention is applicable not only to detection of a single kind but also to concurrent sensing on a large number of kinds in one sample to thereby detect a plurality of kinds concurrently. Further, detection can be performed on a plurality of samples in parallel by use of a plurality of sensors.

The sensor using nanotube-like structures as a channel according to the present invention has strength enough to be used repeatedly. However, the sensor is so inexpensive that the sensor may be made disposable for detection of a dangerous virus or the like.

Although description was made in the aforementioned embodiment about the case where CNTs were used, ultra fine fibers which do not have tube-like shapes can be used.

Although description was made in the aforementioned embodiment about one kind of biosensor having a DNA probe formed therein, for example, three CNT biosensors having SiO2 films respectively may be provided together on a substrate, while a DNA probe, a protein probe and a glycolipid probe are formed on the SiO2 films individually. Thus, different biopolymers (DNA, protein and glycolipid) can be measured concurrently.

Although description was made in the aforementioned embodiment about the case where the surface charge distribution characteristic in DNA was evaluated, the present invention is also applicable to detection of other biopolymers such as sugar chain, RNA, amino acid, sugar, virus, etc. Further, the present invention is also applicable to detection of a change in electron state in the process where protein such as rhodopsin releases protons in response to light, a change in electron state in the structural change of pigment, and so on.

Although an example in which nanotube-like structures were connected to the channel portion of SET was shown in the aforementioned embodiment, nanotube-like structures may be used in the channel portion of FET.

INDUSTRIAL APPLICABILITY

When a microorganism such as a virus enters a human body or another living thing, an antibody against the microorganism begins to interact therewith. Accordingly, any virus an antibody correspondingly thereto is present can be detected from body fluid by the sensor according to the present invention. For example, HA shown in the aforementioned specific Examples is a protein called a spike protein covering the surface of an influenza virus. It is therefore possible to detect the HA by the sensor according to the present invention. Thus, infectious diseases such as influenza, SARS, BSE, etc. can be detected sensitively and fast.

The detection portion of the sensor according to the present invention is small, and an electric signal is used. Accordingly, the detection circuit can be formed into a chip. Thus, the sensor can be used as a portable and inexpensive detector. Accordingly, the sensor can perform testing in the field, and can be provided for any medical institution. Thus, the sensor serves as defense measures of early detection, and also serves as countermeasures against bio-terrorism.

Also in the field of basic science, the sensor according to the present invention realizes detection of bonding strength of intermolecular interaction on the level of one molecule, or classification of viruses or proteins based on current characteristics. Accordingly, a molecule similar to an antibody can be searched, or designed to make a fundamental experiment for drug discovery. In addition, one molecule can be detected with time. Further, the sensor can be used as a basic circuit of a spectroscopic antigen-antibody reaction detection unit.

When the gate electrode or the CNTs of the sensor according to the present invention are modified directly by DNA, complementary DNA can be electrically detected supersensitively. In addition, microorganisms such as infectious viruses, bacteria, etc. can be identified through supersensitive and fast measurement of DNA.

Further, environmental hormones, toxins and inorganic substances can be detected by the sensor according to the present invention. In addition, since the influence of vapor of a sample can be detected, the sensor can be applied to not only fluid but also gas. Accordingly, the sensor can measure concentration of a specific substance such as a harmful substance in the atmosphere or other gases.

The invention claimed is:

1. A sensor comprising:
   a substrate;
   a back gate electrode;
   a source electrode and a drain electrode formed on top of said substrate opposite one another; and
   a channel arranged between said source electrode and said drain electrode, wherein said channel is composed of ultra fine fibers;
   an insulating membrane formed in a portion of said substrate on an opposite side to positions where said source electrode and said drain electrode are located, the back gate electrode formed in a portion of the substrate on a side of said insulating membrane, said insulating membrane being modified by a specific substance that interacts with a substance to be detected, and wherein said substance to be detected is placeable between said modified portion and said back gate electrode.

2. A sensor according to claim 1, wherein said ultra fine fibers are nanotube-like structures.

3. A sensor according to claim 2, wherein a defect is introduced into said nanotube-like structures.

4. A sensor according to claim 1, wherein said specific substance is a biopolymer that interacts with a biopolymer substance to be detected.

5. A sensor according to claim 4, wherein when said substance to be detected is an antigen or an antibody, said specific substance is an antibody or an antigen.

* * * * *